US012780883B2

(12) United States Patent
Schroeder et al.

(10) Patent No.: US 12,780,883 B2
(45) Date of Patent: Nov. 3, 2026

(54) COMPOSITIONS AND METHODS FOR TREATING BREAST CANCER

(71) Applicant: Arizona Board of Regents on Behalf of The University of Arizona, Tucson, AZ (US)

(72) Inventors: Joyce A. Schroeder, Tucson, AZ (US); Benjamin Atwell, Tucson, AZ (US); Angelica Escoto, Tucson, AZ (US)

(73) Assignee: Arizona Board of Regents on Behalf of The University of Arizona, Tucson, AZ (US)

( * ) Notice: Subject to any disclaimer, the term of this patent is extended or adjusted under 35 U.S.C. 154(b) by 531 days.

(21) Appl. No.: 18/232,648

(22) Filed: Aug. 10, 2023

(65) Prior Publication Data

US 2024/0166702 A1 May 23, 2024

Related U.S. Application Data

(63) Continuation-in-part of application No. PCT/US2022/015935, filed on Feb. 10, 2022.

(60) Provisional application No. 63/148,252, filed on Feb. 11, 2021, provisional application No. 63/381,778, filed on Nov. 1, 2022.

(51) Int. Cl.

| | |
|---|---|
| ***A61K 38/00*** | (2006.01) |
| ***A61P 35/00*** | (2006.01) |
| ***C07K 14/00*** | (2006.01) |
| ***C07K 14/47*** | (2006.01) |
| *A61K 39/395* | (2006.01) |

(52) U.S. Cl.

CPC .......... *C07K 14/4703* (2013.01); *A61P 35/00* (2018.01); *A61K 38/00* (2013.01); *A61K 39/395* (2013.01)

(58) Field of Classification Search

None

See application file for complete search history.

(56) References Cited

U.S. PATENT DOCUMENTS

| | | | | |
|---|---|---|---|---|
| 5,804,412 A * | 9/1998 | Gill | .................... | C07K 14/4703 435/325 |
| 2003/0053995 A1 | 3/2003 | Hung et al. | | |
| 2003/0055220 A1 | 3/2003 | Legrain | | |
| 2016/0082082 A1 | 3/2016 | Schroeder | | |
| 2016/0311884 A1 | 10/2016 | Schroeder | | |

OTHER PUBLICATIONS

Hassanpour et al. Review of cancer from perspective of molecular. Journal of Cancer Research and Practice. vol. 4:127-129; (available Jul. 2017). (Year: 2017).*

Jameson et al. Intron 1-Mediated Regulation of EGFR Expression in EGFR-Dependent Malignancies Is Mediated by AP-1 and BET Proteins. Mol Cancer Res; 17(11):2209-2220 (Nov. 2019). (Year: 2019).*

Justice et al. Using the mouse to model human disease: increasing validity and reproducibility, Disease, Models & Mechanisms 9: 101-103 (2016). (Year: 2016).*

Al Qaraghuli et al. Antibody-protein binding and conformational changes: identifying allosteric signaling pathways to engineer a better effector response. Nature Scientific Reports 10:13969, (2020). (Year: 2020).*

Edwards et al. The remarkable flexibility of the human antibody repertoire; isolation of over one thousand different antibodies to a single protein, BLyS. Journal of Molecular Biology 334:103-118; (2003). (Year: 2003).*

Goel et al. Plasticity within the antigen-combining site may manifest as molecular mimicry in the humoral immune response. J. Immunol. 173: 7358-7367; (2004). (Year: 2004).*

Fenton et al. Rheostat positions: A new classification of protein positions relevant to pharmacogenomics Medicinal Chemistry Research 29:1133-1146; (2020). (Year: 2020).*

Bhattacharya et al. Impact of genetic variation on three-dimensional structure and function of proteins PLoS ONE 12(3): e0171355; (2017). (Year: 2017).*

Tokuriki et al. Stability effects of mutations and protein evolvability, Current Opinion in Structural Biology, 19:596-604, (2009). (Year: 2009).*

Guo et al. Protein tolerance to random amino acid change. PNAS USA 101(25):9205-10; (2004). (Year: 2004).*

Bitler et al., "A MUC1 regulates nuclear localization and function of the epidermal growth factor receptor," J Cell Sci 123(10), Abstract only, doi: 10.1242/jcs.062661 (2010).

Bitler et al., "Intracellular MUC1 peptides inhibit cancer progression," Clin Cancer Res 15(1), 100-109, doi: 10.1158/1078-0432. CCR-08-1745 (2009).

Bonifacino et al., "Retromer," Curr. Opin. Cell Biol. 20(4), Abstract only, doi: 10.1016/j.ceb.2008.03.009 (2008).

Brand et al., "Nuclear EGFR as a molecular target in cancer," Radiother Oncol. 108(3), Abstract only, doi:10.1016/j.radonc.2013. 06.010 (2013).

Carlton et al., "Sorting nexin-1 mediates tubular endosome-to-TGN transport through coincidence sensing of high-curvature membranes and 3-phosphoinositides," Current Biology 14, 1791-1800, doi: 10.1016/j.cub.2004.09.077 (2004).

Crunkhorn, "Stapled peptide reactivates p53," Nat. Rev. Drug Discovery 12, 741, doi: 10.1038/nrd4133 (2013).

Dutta et al., "Sorting of Clathrin-Independent Cargo Proteins Depends on Rab35 Delivered by Clathrin-Mediated Endocytosis," Traffic 16(9), Abstract only, doi: 10.1111/tra. 12302 (2015).

Greenwood et al., "LIgl1 prevents metaplastic survival driven by epidermal growth factor dependent migration," Oncotarget 7(38), pp. 60776-60792, doi: 10.18632/oncotarget.11320 (2016).

Gullapalli et al., "A role for sorting nexin 2 in epidermal growth factor receptor down-regulation: evidence for distinct functions of sorting nexin 1 and 2 in protein trafficking," Mol. Biol. of the Cell 15, 2143-2155, doi: 10.1091/mbc.E03-09-0711 (2004).

(Continued)

*Primary Examiner* — Bridget E Bunner

*Assistant Examiner* — Regina M DeBerry

(74) *Attorney, Agent, or Firm* — Cozen O'Connor

(57) ABSTRACT

Compositions and methods for treating breast cancer. The disclosed peptides bind to EGFR and enhance the trafficking of EGFR to lysosomes for destruction. These peptides and small molecule analogs thereof can be used for treating cancer by reducing EGFR levels and/or by activating immune cells.

17 Claims, 15 Drawing Sheets

Specification includes a Sequence Listing.

(56) References Cited

OTHER PUBLICATIONS

Hart et al., "Inactive ERBB receptors cooperate with reactive oxygen species to suppress cancer progression," Mol Ther. 21(11), Abstract only, doi: 10.1038/mt.2013.196 (2013).
Horm et al., "MUC1 drives c-Met-dependent migration and scattering," Mol. Cancer Res. 10(12), Abstract only, doi: 10.1158/1541-7786.MCR-12-0296 (2012).
Hung et al., "Nuclear epidermal growth factor receptor (EGFR) interacts with signal transducer and activator of transcription 5 (STAT5) in activating Aurora—A gene expression," Nucleic Acids Res 36(13), Abstract only, doi: 10.1093/nar/gkn417 (2008).
International Search Report and Written Opinion for PCT/US2022/015935 dated Jul. 18, 2022, 13 pages.
Kurten et al., "Enhanced degradation of EGF receptors by a sorting nexin, SNX1," Science 272, 1008-1010, doi: 10.1126/science.272.5264.1008 (1996).
Lacerda et al., "Mesenchymal stem cells mediate the clinical phenotype of inflammatory breast cancer in a preclinical model," Breast Cancer Res. 17(1), 42, doi: 10.1186/s13058-015-0549-4 (2015).
Lo et al., "Nuclear interaction of EGFR and STAT3 in the activation of the iNOS/NO pathway," Cancer Cell 7(6), Abstract only, doi: 10.1016/j.ccr.2005.05.007 (2005).
Lopez et al., "CD44 attenuates metastatic invasion during breast cancer progression," Cancer Res. 65(15), Abstract only, doi: 10.1158/0008-5472.CAN-05-0863 (2005).
Maisel et al., "Intravesicular epidermal growth factor receptor subject to retrograde trafficking drives epidermal growth factor-dependent migration," Oncotarget 9(5), pp. 6463-6477, doi: 10.18632/oncotarget.23766 (2018).
Maisel et al., "Stapled EGFR peptide reduces inflammatory breast cancer and inhibits additional HER-driven models of cancer," J Transl Med. 17(1), 201, doi: 10.1186/s12967-019-1939-7 (2019).
Nakai et al., "A perspective on anti-EGFR therapies targeting triple-negative breast cancer," Am J Cancer Res 6, Abstract only (2016).
Pochampalli et al., "MUC1 is a novel regulator of ErbB1 receptor trafficking," Oncogene. 26(12), Abstract only, doi: 10.1038/sj.onc.1209976 (2007).
Pochampalli et al., "Transforming growth factor alpha dependent cancer progression is modulated by Muc1," Cancer Res. 67(14), Abstract only, doi: 10.1158/0008-5472.CAN-06-4518 (2007).
Ponde et al., "Treatment of advanced HER2-positive breast cancer: 2018 and beyond," Cancer Treat Rev 67, Abstract only, doi: 10.1016/j.ctrv.2018.04.016 (2018).
Sandgren et al., "Inhibition of mammary gland involution is associated with transforming growth factor alpha but not c-myc-induced tumorigenesis in transgenic mice," Cancer Research 55(17), Abstract only (1995).
Shelly et al., "Polar expression of ErbB-2/HER2 in epithelia. Bimodal regulation by Lin-7," Dev Cell 5(3), Abstract only, doi: 10.1016/j.devcel.2003.08.001 (2003).
Shi et al., "Nuclear EGFR-PKM2 axis induces cancer stem cell-like characteristics in irradiation-resistant cells," Cancer Lett 422, Abstract only, doi: 10.1016/j.canlet.2018.02.028 (2018).
Sorkin et al., "Endocytosis and intracellular trafficking of ErbBs," Exp Cell Res 314(17), pp. 3093-3106, doi:10.1016/j.yexcr.2008.07.029 (2008).
Syrkina et al., "A MUC1 Story: Great Expectations, Disappointments and the Renaissance," Curr. Med. Chem. 26 (3), Abstract only, doi: 10.217 4/0929867324666170817151954 (2019).
Teasdale et al., "Insights into the PX (phox-homology) domain and SNX (sorting nexin) protein families: structures, functions and roles in disease," Biochem J. 441(1), Abstract only, doi: 10.1042/BJ20111226 (2012).
Traynor et al., "Nuclear EGFR protein expression predicts poor survival in early stage non-small cell lung cancer," Lung Cancer 81(1), pp. 138-141, doi: 10.1016/j. lungcan.2013.03.020 (2013).
Waks et al., "Breast Cancer Treatment: A Review," JAMA 321(3), Abstract only, doi: 10.1001/jama.2018.19323 (2019).
Wang et al., "MET inhibitors for targeted therapy of EGFR TKI-resistant lung cancer," J Hematol Oncol. 12(1), 63, doi: 10.1186/s13045-019-0759-9 (2019).

* cited by examiner

Figure 2

A

| | Name: | Sequence: |
|---|---|---|
| SEQ ID NO: 3 | PTD4 | YARAAARQARA |
| SEQ ID NO. 3 | cPTD4 | AcYARAAARQARANH2 |
| SEQ ID NO: 4 | SNX1.1 | YARAAARQARASKDFKNHVIKYLETLLYSQQQLAKYWEAFLFEAKAIS |
| SEQ ID NO: 5 | SNX1.2 | -----------------------------------------/////// |
| SEQ ID NO: 1,2 | SNX1.3 | -----------////--------------------------/////// |
| SEQ ID NO: 6 | SNX1.3M1 | -----------////Q-F-QF--------------------/////// |
| SEQ ID NO: 7 | SNX1.3M2 | -----------////--------QN-FA-------------/////// |
| SEQ ID NO: 8 | SNX1.3M3 | -----------////-------------------QF-Q---/////// |
| SEQ ID NO: 9 | SNX1.3M4 | -----------////------------S-------------/////// |
| SEQ ID NO: 10 | SNX1.4 | -----------////---------------////////////////// |
| SEQ ID NO: 11 | SNX1.5 | ///////----////------RR-RRR-RR-----------/////// |
| SEQ ID NO: 12 | SNX1.6 | ///////----////-----------------RR--RR--R/////// |
| SEQ ID NO: 13 | SNX1.7 | ///////////////-----------------RR--RR--R/////// |
| SEQ ID NO: 14 | SNX1.8 | -----------////-----------------K--------/////// |
| SEQ ID NO: 15 | SNX1.9 | -----------////--------------------D-----/////// |
| SEQ ID NO: 16 | SNX S2 | -----------////-----------------8------5-/////// |
| SEQ ID NO: 17 | SNX S3 | -----------////-5---5--------------------/////// |
| SEQ ID NO: 18 | SNX S4 | -----------////---5---5------------------/////// |
| SEQ ID NO: 19 | SNX S5 | -----------////-------5---5--------------/////// |
| SEQ ID NO: 20 | SNX S6 | -----------////-------------------5---5--/////// |
| SEQ ID NO: 21 | SNX S7 | -----------////-----------8------5-------/////// |
| SEQ ID NO: 22 | SNX S8 | -----------////--5---5-------------------/////// |
| SEQ ID NO: 23 | SNX S9 | -----------////------5---5---------------/////// |
| SEQ ID NO: 24 | SNX S10 | -----------////-------------5---5--------/////// |
| SEQ ID NO: 1,2 | cSNX1.3 | Ac-----------////--------------------------NH2 |

B

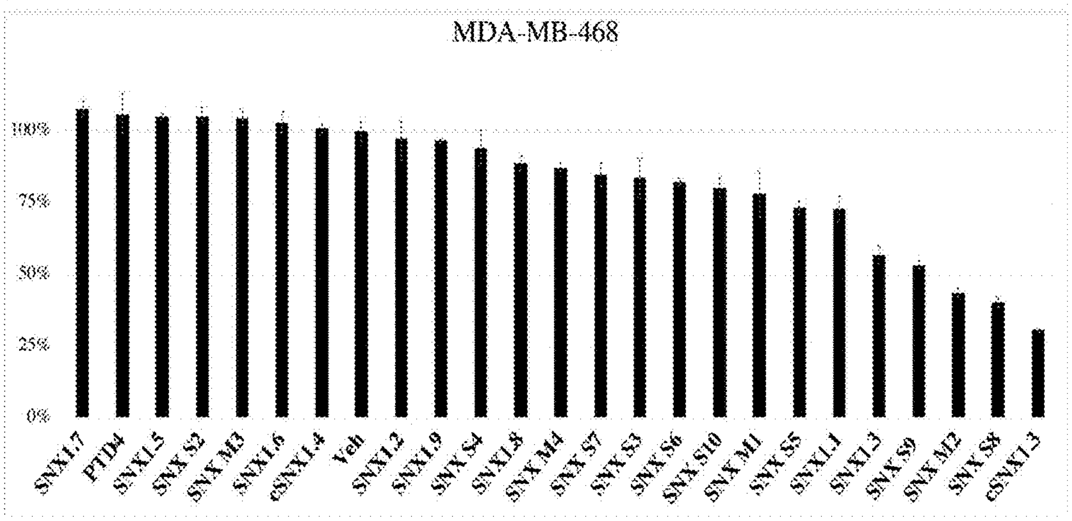

C

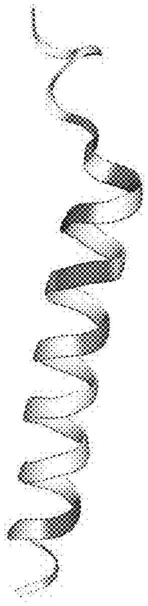

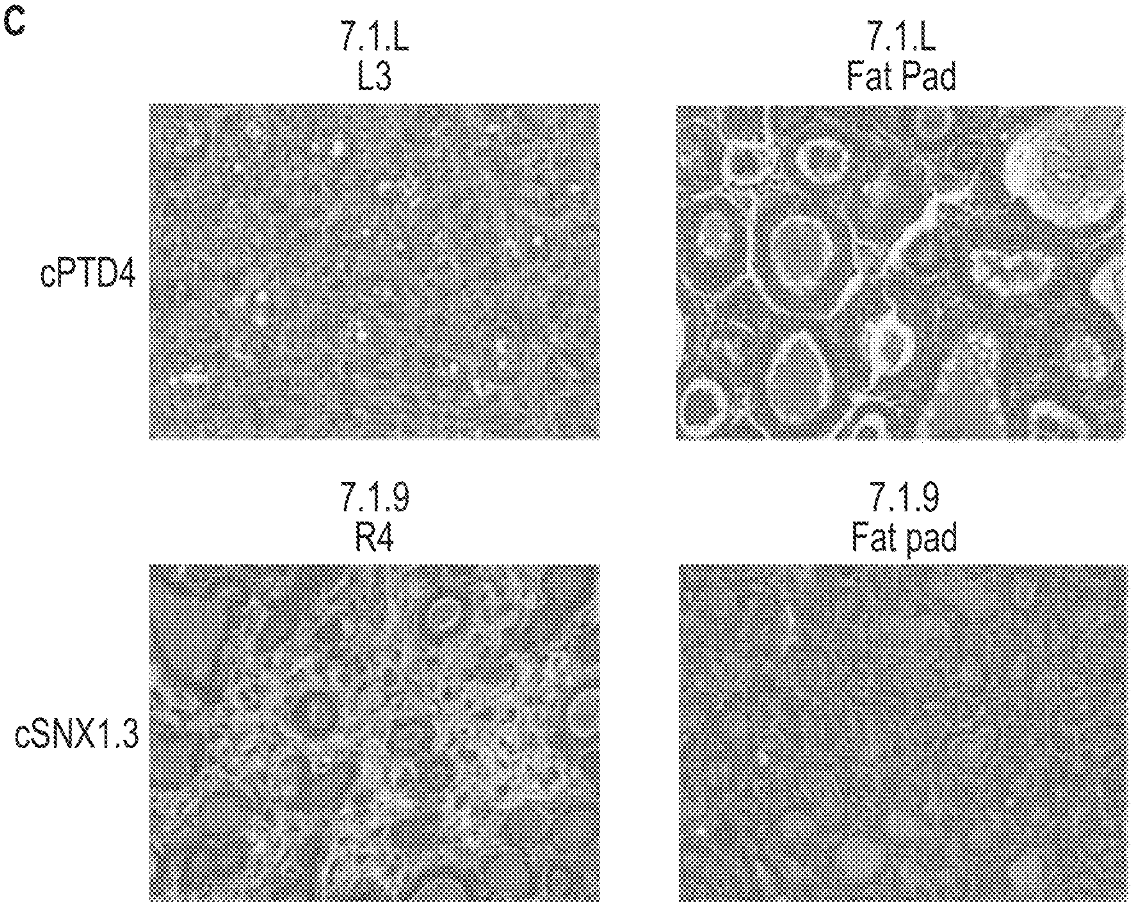
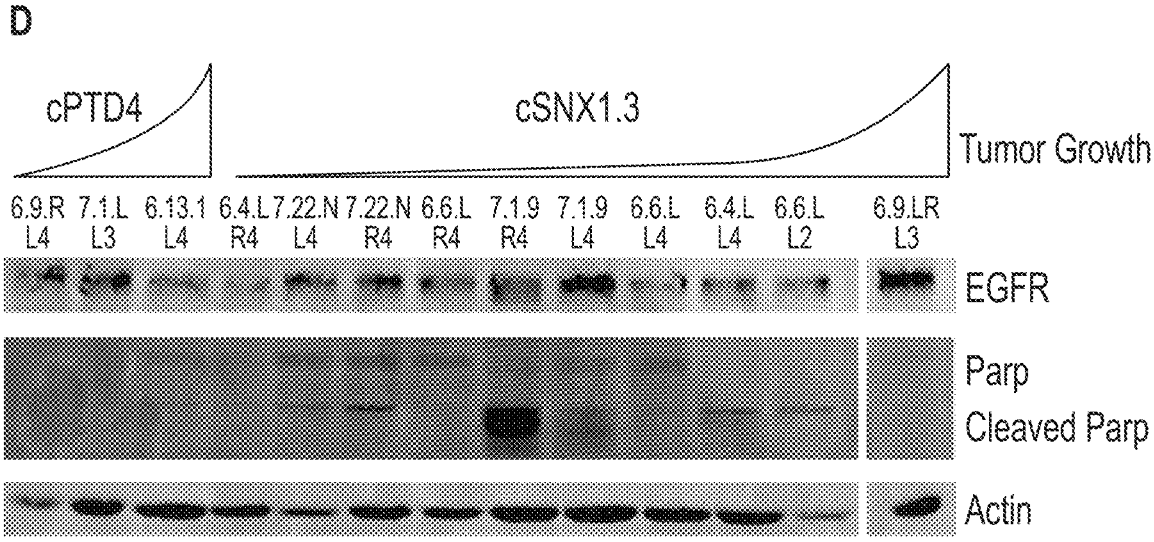
FIG. 3(Continued)

D.
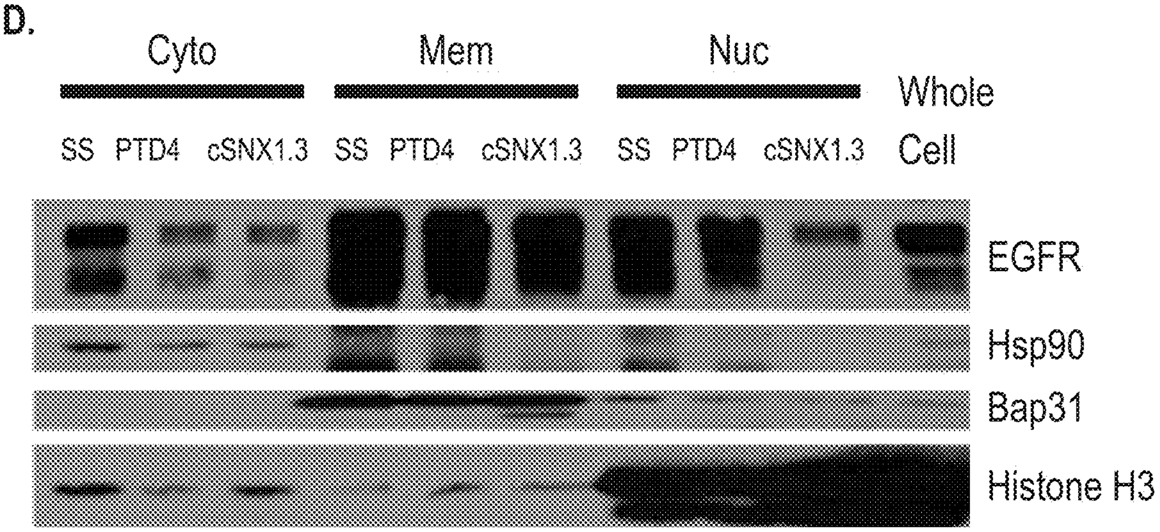
E.
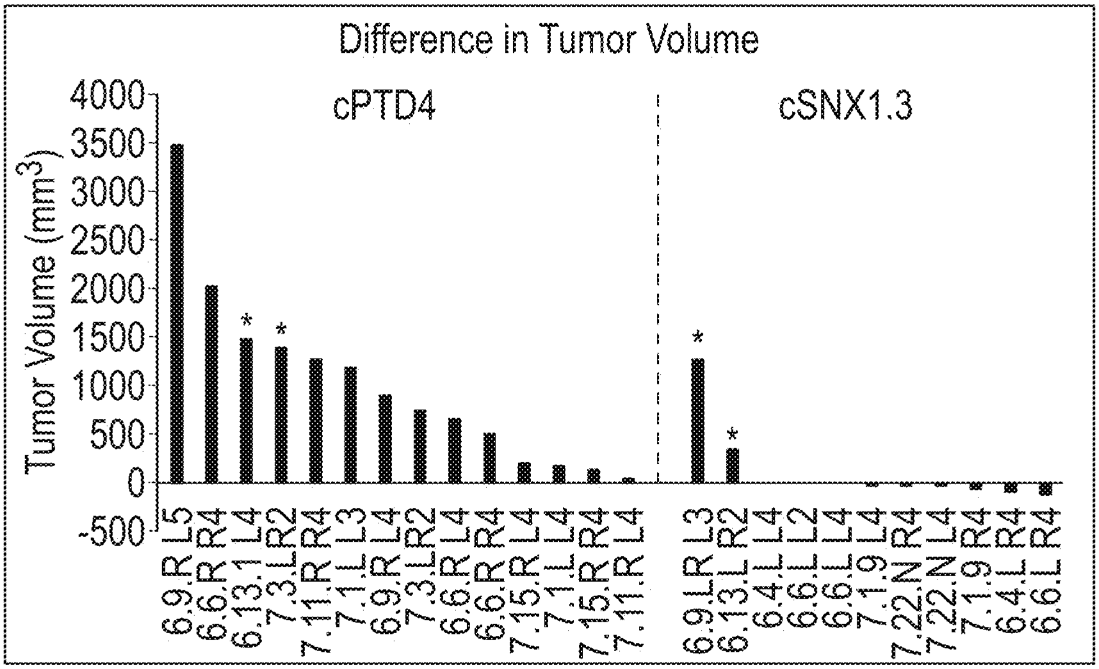
FIG. 7(Continued)

C.
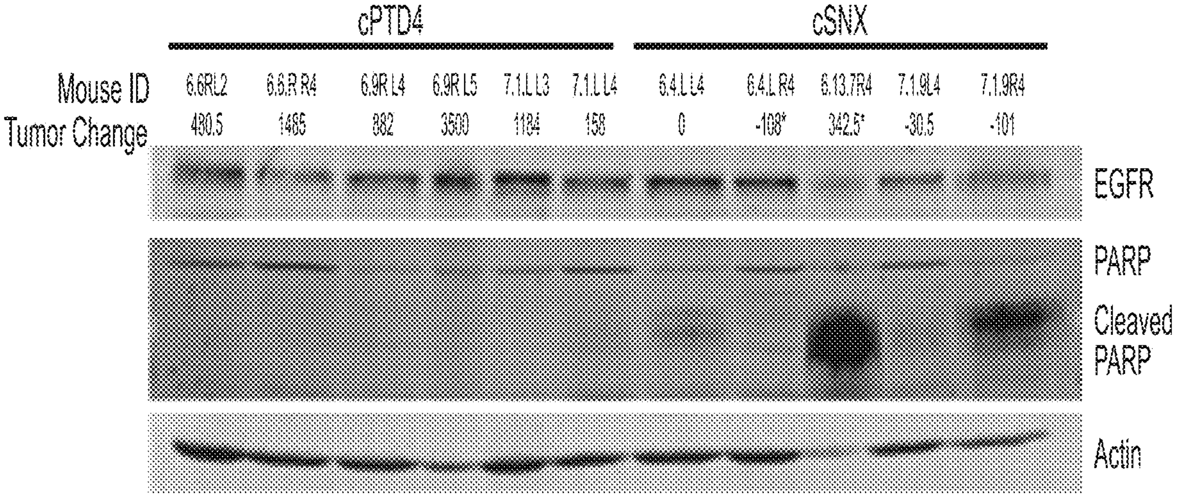
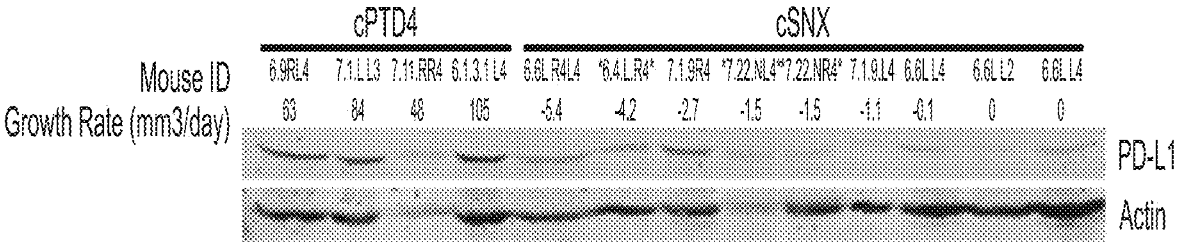
FIG. 8 (Continued)

SEQUENCE LISTING

```
Sequence total quantity: 24
SEQ ID NO: 1            moltype = AA  length = 37
FEATURE                 Location/Qualifiers
source                  1..37
                        mol_type = protein
                        organism = synthetic construct
SEQUENCE: 1
YARAAARQAR AKNHVIKYLE TLLYSQQQLA KYWEAFL                          37

SEQ ID NO: 2            moltype = AA  length = 37
FEATURE                 Location/Qualifiers
source                  1..37
                        mol_type = protein
```

```
                        organism = synthetic construct
SEQUENCE: 2
YARAAARQAR AKNHVIKYLE TLLYSQQQLA KYWEAFL                      37

SEQ ID NO: 3            moltype = AA  length = 11
FEATURE                 Location/Qualifiers
source                  1..11
                        mol_type = protein
                        organism = synthetic construct
SEQUENCE: 3
YARAAARQAR A                                                  11

SEQ ID NO: 4            moltype = AA  length = 48
FEATURE                 Location/Qualifiers
source                  1..48
                        mol_type = protein
                        organism = synthetic construct
SEQUENCE: 4
YARAAARQAR ASKDFKNHVI KYLETLLYSQ QQLAKYWEAF LPEAKAIS          48

SEQ ID NO: 5            moltype = AA  length = 41
FEATURE                 Location/Qualifiers
source                  1..41
                        mol_type = protein
                        organism = synthetic construct
SEQUENCE: 5
YARAAARQAR ASKDFKNHVI KYLETLLYSQ QQLAKYWEAF L                 41

SEQ ID NO: 6            moltype = AA  length = 37
FEATURE                 Location/Qualifiers
source                  1..37
                        mol_type = protein
                        organism = synthetic construct
SEQUENCE: 6
YARAAARQAR AQNFVQFYLE TLLYSQQQLA KYWEAFL                      37

SEQ ID NO: 7            moltype = AA  length = 37
FEATURE                 Location/Qualifiers
source                  1..37
                        mol_type = protein
                        organism = synthetic construct
SEQUENCE: 7
YARAAARQAR AKNHVIKYQN TFAYSQQQLA KYWEAFL                      37

SEQ ID NO: 8            moltype = AA  length = 37
FEATURE                 Location/Qualifiers
source                  1..37
                        mol_type = protein
                        organism = synthetic construct
SEQUENCE: 8
YARAAARQAR AKNHVIKYLE TLLYSQQQLA QFWQAFL                      37

SEQ ID NO: 9            moltype = AA  length = 37
FEATURE                 Location/Qualifiers
source                  1..37
                        mol_type = protein
                        organism = synthetic construct
SEQUENCE: 9
YARAAARQAR AKNHVIKYLE TLLSSQQQLA KYWEAFL                      37

SEQ ID NO: 10           moltype = AA  length = 26
FEATURE                 Location/Qualifiers
source                  1..26
                        mol_type = protein
                        organism = synthetic construct
SEQUENCE: 10
YARAAARQAR AKNHVIKYLE TLLYSQ                                  26

SEQ ID NO: 11           moltype = AA  length = 30
FEATURE                 Location/Qualifiers
source                  1..30
                        mol_type = protein
                        organism = synthetic construct
SEQUENCE: 11
QARAKNHVIR RLRRRLRRQQ QLAKYWEAFL                              30

SEQ ID NO: 12           moltype = AA  length = 30
FEATURE                 Location/Qualifiers
source                  1..30
```

```
                        mol_type = protein
                        organism = synthetic construct
SEQUENCE: 12
QARAKNHVIK YLETLLYSQQ QRRKYRRAFR                                30

SEQ ID NO: 13           moltype = AA  length = 23
FEATURE                 Location/Qualifiers
source                  1..23
                        mol_type = protein
                        organism = synthetic construct
SEQUENCE: 13
VIKYLETLLY SQQQRRKYRR AFR                                       23

SEQ ID NO: 14           moltype = AA  length = 37
FEATURE                 Location/Qualifiers
source                  1..37
                        mol_type = protein
                        organism = synthetic construct
SEQUENCE: 14
YARAAARQAR AKNHVIKYLE TLLYSQQQKA KYWEAFL                        37

SEQ ID NO: 15           moltype = AA  length = 37
FEATURE                 Location/Qualifiers
source                  1..37
                        mol_type = protein
                        organism = synthetic construct
SEQUENCE: 15
YARAAARQAR AKNHVIKYLE TLLYSQQQLA KDWEAFL                        37

SEQ ID NO: 16           moltype = AA  length = 37
FEATURE                 Location/Qualifiers
source                  1..37
                        mol_type = protein
                        organism = synthetic construct
MOD_RES                 36
                        note = (S)-2-(((9H-flouren-9-yl) methoxy)
                         caronylamino)-2-methyl-hept-6-enoic acid
MOD_RES                 29
                        note = (R)-2-(((9H-flouren-9-yl) methoxy)
                         caronylamino)-2-methyl-dec-9-enoic acid
SEQUENCE: 16
YARAAARQAR AKNHVIKYLE TLLYSQQQXA KYWEAXL                        37

SEQ ID NO: 17           moltype = AA  length = 37
FEATURE                 Location/Qualifiers
source                  1..37
                        mol_type = protein
                        organism = synthetic construct
MOD_RES                 13
                        note = (S)-2-(((9H-flouren-9-yl) methoxy)
                         caronylamino)-2-methyl-hept-6-enoic acid
MOD_RES                 17
                        note = (S)-2-(((9H-flouren-9-yl) methoxy)
                         caronylamino)-2-methyl-hept-6-enoic acid
SEQUENCE: 17
YARAAARQAR AKXHVIXYLE TLLYSQQQLA KYWEAFL                        37

SEQ ID NO: 18           moltype = AA  length = 37
FEATURE                 Location/Qualifiers
source                  1..37
                        mol_type = protein
                        organism = synthetic construct
MOD_RES                 15
                        note = (S)-2-(((9H-flouren-9-yl) methoxy)
                         caronylamino)-2-methyl-hept-6-enoic acid
MOD_RES                 19
                        note = (S)-2-(((9H-flouren-9-yl) methoxy)
                         caronylamino)-2-methyl-hept-6-enoic acid
SEQUENCE: 18
YARAAARQAR AKNHXIKYXE TLLYSQQQLA KYWEAFL                        37

SEQ ID NO: 19           moltype = AA  length = 37
FEATURE                 Location/Qualifiers
source                  1..37
                        mol_type = protein
                        organism = synthetic construct
MOD_RES                 19
                        note = (S)-2-(((9H-flouren-9-yl) methoxy)
                         caronylamino)-2-methyl-hept-6-enoic acid
```

```
MOD_RES                 23
                        note = (S)-2-(((9H-flouren-9-yl) methoxy)
                         caronylamino)-2-methyl-hept-6-enoic acid
SEQUENCE: 19
YARAAARQAR AKNHVIKYXE TLXYSQQQLA KYWEAFL                          37

SEQ ID NO: 20           moltype = AA  length = 37
FEATURE                 Location/Qualifiers
source                  1..37
                        mol_type = protein
                        organism = synthetic construct
MOD_RES                 31
                        note = (S)-2-(((9H-flouren-9-yl) methoxy)
                         caronylamino)-2-methyl-hept-6-enoic acid
MOD_RES                 35
                        note = (S)-2-(((9H-flouren-9-yl) methoxy)
                         caronylamino)-2-methyl-hept-6-enoic acid
SEQUENCE: 20
YARAAARQAR AKNHVIKYLE TLLYSQQQLA XYWEXFL                          37

SEQ ID NO: 21           moltype = AA  length = 37
FEATURE                 Location/Qualifiers
source                  1..37
                        mol_type = protein
                        organism = synthetic construct
MOD_RES                 30
                        note = (S)-2-(((9H-flouren-9-yl) methoxy)
                         caronylamino)-2-methyl-hept-6-enoic acid
MOD_RES                 23
                        note = (R)-2-(((9H-flouren-9-yl) methoxy)
                         caronylamino)-2-methyl-dec-9-enoic acid
SEQUENCE: 21
YARAAARQAR AKNHVIKYLE TLXYSQQQLX KYWEAFL                          37

SEQ ID NO: 22           moltype = AA  length = 37
FEATURE                 Location/Qualifiers
source                  1..37
                        mol_type = protein
                        organism = synthetic construct
MOD_RES                 14
                        note = (S)-2-(((9H-flouren-9-yl) methoxy)
                         caronylamino)-2-methyl-hept-6-enoic acid
MOD_RES                 18
                        note = (S)-2-(((9H-flouren-9-yl) methoxy)
                         caronylamino)-2-methyl-hept-6-enoic acid
SEQUENCE: 22
YARAAARQAR AKNXVIKXLE TLLYSQQQLA KYWEAFL                          37

SEQ ID NO: 23           moltype = AA  length = 37
FEATURE                 Location/Qualifiers
source                  1..37
                        mol_type = protein
                        organism = synthetic construct
MOD_RES                 18
                        note = (S)-2-(((9H-flouren-9-yl) methoxy)
                         caronylamino)-2-methyl-hept-6-enoic acid
MOD_RES                 22
                        note = (S)-2-(((9H-flouren-9-yl) methoxy)
                         caronylamino)-2-methyl-hept-6-enoic acid
SEQUENCE: 23
YARAAARQAR AKNHVIKXLE TXLYSQQQLA KYWEAFL                          37

SEQ ID NO: 24           moltype = AA  length = 37
FEATURE                 Location/Qualifiers
source                  1..37
                        mol_type = protein
                        organism = synthetic construct
MOD_RES                 25
                        note = (S)-2-(((9H-flouren-9-yl) methoxy)
                         caronylamino)-2-methyl-hept-6-enoic acid
MOD_RES                 29
                        note = (S)-2-(((9H-flouren-9-yl) methoxy)
                         caronylamino)-2-methyl-hept-6-enoic acid
SEQUENCE: 24
YARAAARQAR AKNHVIKYLE TLLYXQQQXA KYWEAFL                          37
```

COMPOSITIONS AND METHODS FOR TREATING BREAST CANCER

CROSS-REFERENCE TO RELATED APPLICATIONS

This application claims benefit of priority to U.S. Provisional Patent Application No. 63/381,778 filed on Nov. 1, 2022. This application is also a continuation-in-part (CIP) application of International patent application PCT/US2022/015935 filed Feb. 10, 2022, which claims priority to U.S. Provisional Patent Application No. 63/148,252 filed on Feb. 11, 2021. The contents of all of the above-mentioned applications are incorporated herein by reference in their entirety.

GOVERNMENT RIGHTS

This invention was made with government support under Grant No. W81XWH-18-1-0663, awarded by ARMY/MRMC. The government has certain rights in the invention.

SEQUENCE LISTING

The instant application contains a Sequence Listing which has been submitted via Patent Center and is hereby incorporated by reference in its entirety. Said .xml copy, created on Sep. 8, 2023 is named UOAZP2029US_00588500, and is 30,348 bytes in size.

BACKGROUND

Hormone receptor negative breast cancer represents approximately 40% of all breast cancer cases and is the most aggressive and metastatic. Waks, et al. (2019). Triple-negative breast cancer is cancer that tests negative for estrogen receptors, progesterone receptors, and excess HER2 protein. The HER family of tyrosine kinase receptors is highly prevalent within hormone negative disease, and in some cases, antibody-based therapeutics are highly effective. In HER2 negative, but HER1 or HER3 positive cases, HER-targeted treatments are ineffective, and it is clear these receptors can function in noncanonical ways. For example, in metastatic and therapeutic-resistant patient samples, HER1 is not found on the cell surface, but instead is localized to the nucleus. Traynor et al. (2013). HER1/EGFR can undergo retrotranslocation (rt-EGFR) to long-lived intracellular vesicles and the nucleus, where it can both continue to signal and act directly as a transcriptional cofactor. Maisel, et al., (2018).

It has been shown that in certain breast cancer cells, activated EGFR receptors can undergo retrograde trafficking (Retrograde Trafficked EGFR; rt-EGFR) and reside intracellularly instead of on the cell surface where it may be targeted by antibody-based therapeutics. In this way, EGFR is maintained in long-lived endosomes that do not get targeted to the lysosome for degradation, and also undergoes nuclear translocation where it functions directly as a transcriptional cofactor. Rt-EGFR is driven to this route by multiple mechanisms, including a loss of epithelial polarity and basolateral targeting, and colocalization with the oncogene MUC1. Rt-EGFR may promote a cancer stem cell-like phenotype with increased survival and migration as well as new gene transcription. Once in the nucleus, EGFR may function as a transcriptional cofactor for STAT3 and STAT5, regulating the expression of genes that promote proliferation, survival and stemness. Rt-EGFR is correlated with metastatic progression, patient mortality and therapeutic resistance and may regulate the expression of a number of oncogenes that drive metastasis and survival.

Targeting of EGFR and other RTKs has historically focused on two areas: either with small molecule inhibitors of the tyrosine kinase activity (TKIs), or via specific antibodies that bind to the cell surface-localized receptor to either alter receptor activation, induce its internalization and degradation, or to activate the patient's immune system against antibody-bound cells. While these approaches have had stunning success in certain types of cancers, such as HER2 positive breast cancer and EGFR-positive lung cancer, they have failed to impact EGFR-expressing breast cancers. Cancers caused by other oncogenic receptors such as the Met receptor and HER3 also respond poorly to such therapeutics.

Patients diagnosed with metastatic Triple Negative Breast Cancer (TNBC) are faced with a median overall survival of only 13-18 months. These aggressive and deadly cancers fail to respond to targeted therapeutics, including immune checkpoint therapies, anti-growth factor receptor antibodies and kinase inhibitors, and represent a strong unmet clinical need. The immune microenvironment of TNBC is heterogeneous and tumor promoting, comprised of a variety of CD8+/CD4+ T cells, B cells, Tregulatory cells and tumor promoting M2/M1 macrophage ratios. The immune microenvironment of the primary and metastatic tumors can be driven by oncogenes such as Receptor Tyrosine Kinases, yet the mechanism of driving this immune suppression in TNBC is unclear. It is essential to understand this effect as activation of the immune microenvironment, specifically Cytotoxic T Lymphocytes (CTLs) and Natural Killer cells (NK cells) can induce tumor killing and prevent metastatic spread and survival.

The HER family of tyrosine kinase receptors (RTKs, including EGFR, HER2 and HER3) is highly prevalent in breast cancer, and in some cases, antibody-based therapeutics against these tyrosine kinase receptors (i.e., Trastuzumab) are effective. However, in HER2 negative, but EGFR and HER3 positive breast cancer, antibody-based treatments have not shown efficacy. In addition, while Tyrosine Kinase Inhibitors (TKIs) work well in many cancers, such as lung, head and neck and colon cancer, they have failed to be impactful in breast cancer. EGFR is amplified and/or overexpressed in 22% of all breast cancers. In TNBC, EGFR is a marker for the basal subtype and overexpressed in over 70% of all TNBC. In addition, TNBC and basal subtyped tumor are frequently immune suppressed, with low tumor infiltrating lymphocytes. This subtype of TNBC, termed BLIS (basal-like immune suppressed) have the worst prognosis of all breast cancer subtypes. Importantly, the immune profile of TNBC is correlated with survival; patients with higher tumor infiltrating lymphocytes have overall better outcomes. Yet metTNBC with high EGFR expression is correlated with an immune suppressive microenvironment, upregulation of PDL1 and suppression of NK cells.

SUMMARY

The present disclosure provides compositions and methods for treating breast cancer. In one embodiment, it is disclosed that blocking of rt-EGFR may induce the degradation of EGFR. In another embodiment, it is disclosed that blocking of rt-EGFR may result in loss of cell survival and migratory capacity, which, in turn, induces tumor regression. In another embodiment, it is disclosed that cancer-specific trafficking event can be therapeutically targeted, which results in inhibition of nuclear retrotranslocation of EGFR and other similarly regulated RTKs, such as HER3 and c-Met.

A search for molecular drivers of metTNBC shows that EGFR is overexpressed in greater than 70% of Triple Negative Breast Cancer (TNBC), which is associated with poor outcomes, and exhibits an immune suppressive microenvironment. Yet, anti-EGFR antibody- and tyrosine kinase inhibitor-based therapies have failed to have impact. One aspect of EGFR biology that has not been targeted is its role as a transcription factor, where the nuclear translocation of EGFR that occurs during metastatic progression can drive a novel suite of genes that promotes tumor survival. The nuclear translocation of EGFR is regulated by its interaction with Sorting Nexin 1 (Snx1), an integral membrane protein that regulates vesicular trafficking. To investigate the role of nuclear EGFR, a cell penetrating peptide that blocks the ability of Snx1 to bind to EGFR, cSNX1.3, has been developed.

Treatment with cSNX1.3 results in a unique set of changes to gene expression that reflect a change to the immune and metastatic potential of cancer. Evaluation of tumors after treatment (both human TNBC in vitro and mouse tumors in vivo) show that cSNX1.3 treatment results in activation of an immune surveillance microenvironment, including the activation of both CTLs and NK cells and an increase in the M1/M2 macrophage polarity (with M1 being tumor suppressive and M2 being tumor promoting). This unique approach to targeting RTK function in TNBC has the potential of not only treating the primary tumor but also inhibiting metastatic progression, as NK cells have the capacity to seek out and destroy cells surviving in metastatic niches throughout the body.

In one embodiment, a composition is disclosed, which comprises a molecule capable of binding to an epidermal growth factor receptor (EGFR) in a cell, wherein the molecule, when bound to the EGFR, inhibits retrotranslocation of the EGFR to the nucleus. In another embodiment, the disclosed composition may be used in a method for treating cancer, which includes delivering the disclosed composition to a subject. In another embodiment, a pharmaceutical composition is disclosed which comprises a therapeutically effective amount of a molecule capable of binding to an epidermal growth factor receptor (EGFR) in a cell of the subject, wherein said molecule, when bound to the EGFR, inhibits retrotranslocation of the EGFR to the nucleus.

In one aspect, this molecule binds to the kinase domain of the EGFR. In another aspect, wherein this molecule is also capable of inhibiting migration driven by a second receptor tyrosine kinase (RTK) which is different from EGFR. Examples of the RTK include but are not limited to C-Met, HER3 and HER4. In another aspect, the second RTK undergoes clathrin-dependent endocytosis.

In another embodiment, the molecule is a member selected from the group consisting of a peptide, an oligonucleotide, a non-peptide organic molecule and combination thereof. In one aspect, the molecule may comprise a peptide having a sequence at least 90% identical to the sequence of SEQ ID NO: 1 or SEQ ID NO: 2. For instance, 1 amino acid, 2 amino acids, or 3 amino acids can be mutated from the sequence of SEQ ID NO: 1 or SEQ ID NO: 2. In another aspect, the molecule is the peptide having the sequence of SEQ ID NO: 1 or SEQ ID NO: 2.

In another embodiment, the pharmaceutical composition causes regression of tumors when administered to a patient. In one aspect, the disclosed molecule blocks retrotranslocation of EGFR, and therefore, it behaves differently from a conventional kinase inhibitor. In another aspect, the disclosed molecule cause cell death in cancer cells but does not cause observable toxicity in normal non-cancer cells.

In one aspect, the cancer is a triple-negative breast cancer. In another aspect, the cancer is an EGFR-dependent cancer. In another aspect, the dosage is 1 mg to 200 mg per kg body weight of the subject.

In another embodiment, disclosed here are platforms and methods to identify small molecules that can mimic the activity of cSNX1.3. high throughput screen (HTS).

In an aspect, a method of treating cancer in a patient in need thereof is described, comprising administering the disclosed composition to the patient. In an embodiment, the cancer is metastatic triple negative breast cancer. In an embodiment, the composition activates immune cells in the patient. In an embodiment, the immune cells comprise at least one member selected from the group consisting of Cytotoxic T Lymphocytes (CTLs), Natural Killer cells (NK cells) and macrophages. In an embodiment, the activated immune cells induce tumor killing and prevent metastatic spread of the cancer.

BRIEF DESCRIPTION OF THE DRAWINGS

FIG. 2 (SEQ ID NO:3-24) shows that cSNX1.3 peptide inhibits cell viability in MDA-MB-468 cells. A. Peptide sequence alignment of modified and stabilized peptides (–) indicates conserved residues, (/) indicates a deleted residue. Modified residues used for staples are (S)-2-(((9H-flouren-9-yl) methoxy) caronylamino)-2-methyl-hept-6-enoic acid (5) and (R)-2-(((9H-flouren-9-yl) methoxy) caronylamino)-2-methyl-dec-9-enoic acid (8). PTD4=Protein Transduction Domain. Ac=acetylation of 5' end and NH2=amidation of 3' end. B. MDA-MB-468 cells were treated with 10 μM of the indicated peptide for 3 days. Cell viability was measured using an MTT assay. Vehicle control represents 100%. C. A predicted peptide structure of SNX1.3 was generated using SWISSMODEL with negative (blue) and positive (red) residues highlighted.

DETAILED DESCRIPTION

Figure 1:
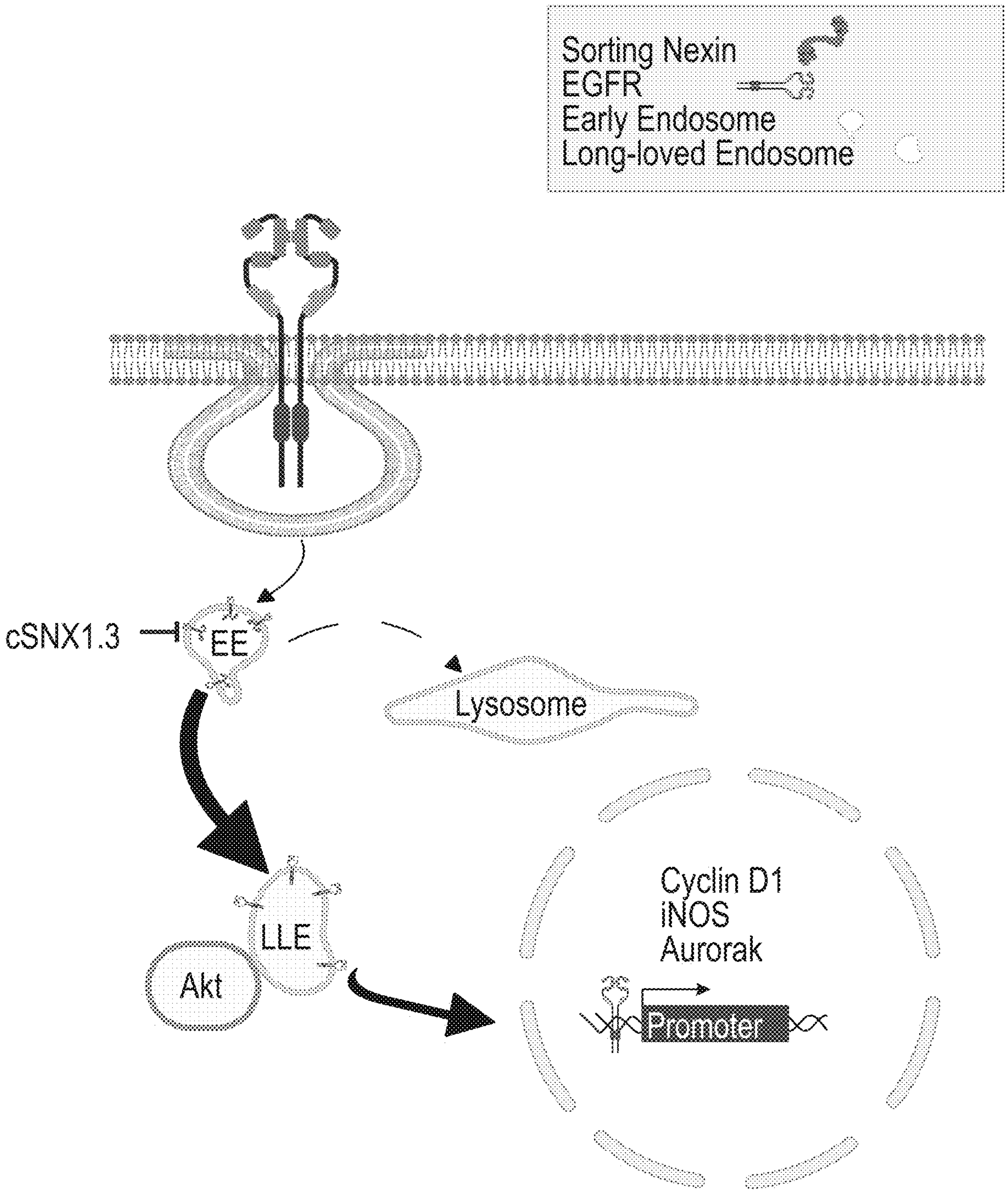
FIG. 1 illustrates retrotranslocation of the Epidermal Growth Factor Receptor. Under normal conditions, EGFR is internalized and routed to the lysosome upon ligand binding (dashed arrow). Under conditions of loss of polarity, interaction with MUC1 or loss of basolateral targeting, EGFR is maintained in both long-lived EEA1-positive endosomes and traffics to the nucleus (retrotranslocation—rt). Rt-EGFR supports cancer stem cell phenotypes including migration and survival.

The present disclosure provides compositions and methods for treating breast cancer. In one embodiment, it is disclosed that blocking of rt-EGFR causes loss of cell survival and migratory capacity, which, in turn, induces tumor regression. In one aspect, during EGF-induced retrotranslocation, EGFR interacts with Sorting Nexin 1 and 2.

In normal epithelial cells, ligand stimulation of EGFR results in clathrin-mediated endocytosis and trafficking to the lysosome for degradation. This trafficking is regulated by multiple protein complexes, one of which involves a set of proteins called the Sorting Nexins (SNX).

In one embodiment, a peptide mimic of the EGFR binding domain of Sorting Nexin 1 (cSNX1.3) is disclosed. In one aspect, this peptide induces cell death in a cancer-specific manner and reduces the retrotranslocation of EGFR to the nucleus. In another aspect, cSNX1.3 competitively inhibits the interaction between the Sorting Nexin 1 Bar domain and the cytoplasmic domain of EGFR. This is correlated with a significant reduction in cell survival in mammosphere assays and an induction of apoptosis in an EGF-dependent manner. In another aspect, retrograde trafficking of receptor tyrosine kinases in breast cancer may be an essential component of their ability to induce cell survival and migration.

Another embodiment of the present disclosure is illuminating the mechanism by which RTKs undergo retrotranslocation in breast cancer.

Another embodiment of the present disclosure is identification of small molecules (or compounds) to target this RT-EGFR phenomenon. Examples of small molecules (or compounds) may include but are not limited to non-peptide organic molecules, peptides, oligonucleotides, or analogs thereof.

Yet another embodiment of the present disclosure is showing therapeutic activity of the identified small molecules on mouse models of breast cancer, and for clinical trials in humans.

In another embodiment, a composition for treating cancer is disclosed, which contains a molecule capable of binding to EGFR in a cell and reducing its retrotranslocation to the nucleus. In one aspect, the molecule may be selected from the group consisting of a peptide, an oligonucleotide, a non-peptide organic molecule and combination thereof.

In another embodiment, a method for treating cancer is disclosed, which includes delivering the composition containing the disclosed molecule to a patient in need thereof.

In another embodiment, a pharmaceutical composition comprising the disclosed compositions and a pharmaceutically acceptable carrier or excipient is disclosed.

In another embodiment, the composition is effective for treating breast cancer, as well as other cancer types in which EGFR is implicated.

In another embodiment, the composition is effective for treating triple negative breast cancer.

In another embodiment, the pharmaceutical composition comprises a therapeutically effective amount of the disclosed molecule and a pharmaceutically acceptable carrier or excipient.

In another embodiment, small molecules that bind to the EGFR or other RTKs and inhibits their retrotranslocation may be identified in high throughput screening using platforms and methods known in the art. See e.g., Stockwell, et al., Chemistry and Biology 1999, Vol 6 No 2, 71-83; and Landry, et al., Int Drug Discov. 2011 Dec. 8-13.

The articles "a," "an" and "the" are used to refer to one or more than one (i.e., to at least one) of the grammatical object of the article.

The terms "comprise", "comprising", "including" "containing", "characterized by", and grammatical equivalents thereof are used in the inclusive, open sense, meaning that additional elements are not expressly mentioned but may be included. It is not intended to be construed as "consists of only."

The term "subject" or "patient" as used herein is intended to include animals. Examples of subjects include but are not limited to mammals, e.g., humans, apes, monkeys, dogs, cows, horses, pigs, sheep, goats, cats, mice, rabbits, rats, and transgenic non-human animals. In an embodiment, the subject is a human.

The term "biological sample" or "sample" encompasses a variety of sample types obtained from an organism. The term encompasses bodily fluids such as blood, saliva, serum, plasma, urine and other liquid samples of biological origin, and solid samples, such as a nasopharyngeal swab, a biopsy specimen or tissue cultures or cells derived therefrom and the progeny thereof.

The terms "polypeptide," "peptide" and "protein" may be used interchangeably in this disclosure. The terms "oligonucleotide," and "polynucleotide" may also be used interchangeably in this disclosure.

Various embodiments of the present disclose are listed to illustrate but not to limit the disclosure:

Item 1. A composition comprising a molecule capable of binding to an epidermal growth factor receptor (EGFR) in a cell, wherein said molecule, when bound to the EGFR, inhibits retrotranslocation of the EGFR to nucleus.

Item 2. The composition of Item 1, wherein the molecule binds to the kinase domain of the EGFR.

Item 3. The composition of any of preceding Items, wherein the molecule is further capable of inhibiting migration driven by a second receptor tyrosine kinase (RTK), said second receptor tyrosine kinase being different from EGFR.

Item 4. The composition of any of preceding Items, wherein said second RTK undergoes clathrin-dependent endocytosis.

Item 5. The composition of any of preceding Items, wherein the RTK is a member selected from the group consisting of C-Met, HER3 and HER4.

Item 6. The composition of any of preceding Items, wherein the molecule is a member selected from the group consisting of a peptide, an oligonucleotide, a non-peptide organic molecule and combination thereof.

Item 7. The composition of any of preceding Items, wherein the molecule causes regression of tumors.

Item 8. The composition of any of preceding Items, wherein the molecule does not cause observable toxicity in normal non-cancer cells.

Item 9. The composition of any of preceding Items, wherein said molecule comprises a peptide having a sequence at least 90% identical to the sequence of SEQ ID NO: 1.

Item 10. The composition of any of preceding Items, wherein said molecule is a peptide having the sequence of SEQ ID NO: 1.

Item 11. The composition of any of preceding Items, wherein said molecule comprises a peptide having a sequence at least 90% identical to the sequence of SEQ ID NO: 2.

Item 12. The composition of any of preceding Items, wherein said molecule is a peptide having the sequence of SEQ ID NO: 2.

Item 13. A method for treating cancer, comprising delivering a composition to a subject, the composition comprising a molecule capable of binding to an epidermal growth factor receptor (EGFR) in a cell of the subject, wherein said molecule, when bound to the EGFR, inhibits retrotranslocation of the EGFR to nucleus.

Item 14. The method of Item 13, wherein the cancer is a triple-negative breast cancer.

Item 15. The method of Items 13-14, wherein the cancer is an EGFR-dependent cancer.

Item 16. The method of Items 13-15, wherein the molecule is capable of inhibiting migration driven by a second receptor tyrosine kinase (RTK), said second receptor tyrosine kinase being different from EGFR.

Item 17. The method of Items 13-16, wherein the RTK is a member selected from the group consisting of C-Met, HER3 and HER4.

Item 18. The method of Items 13-17, wherein the molecule does not cause observable toxicity in normal non-cancer cells.

Item 19. The method of Items 13-18, wherein the molecule causes regression of tumors.

Item 20. The method of Items 13-19, wherein said molecule comprises a peptide having a sequence at least 90% identical to the sequence of SEQ ID NO: 1.

Item 21. The method of Items 13-20, wherein said molecule is a peptide having the sequence of SEQ ID NO: 1.

Item 22. The method of Items 13-21, wherein said molecule comprises a peptide having a sequence at least 90% identical to the sequence of SEQ ID NO: 2.

Item 23. The method of Items 13-22, wherein said molecule is a peptide having the sequence of SEQ ID NO: 2.

Item 24. The method of Items 13-23, wherein the dosage is from 1 mg to 200 mg per kg body weight of the subject.

Item 25. A pharmaceutical composition comprising a therapeutically effective amount of a molecule capable of binding to an epidermal growth factor receptor (EGFR) in a cell of the subject, wherein said molecule, when bound to the EGFR, inhibits retrotranslocation of the EGFR to nucleus.

Item 26. The pharmaceutical composition of Item 25, wherein said molecule is a peptide having the sequence of SEQ ID NO: 1.

Item 27. The pharmaceutical composition of Items 25-26, wherein said molecule is a peptide having the sequence of SEQ ID NO: 2.

Item 28. The pharmaceutical composition of Items 25-27, further comprising a pharmaceutically acceptable carrier or excipient.

EXAMPLES

The disclosure will now be illustrated with working examples, and which is intended to illustrate the working of disclosure and not intended to restrict any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Example 1 Peptides Mimicking the EGFR Interaction Domain of Sorting Nexin 1 Inhibit Retrotranslocation of EGFR In normal epithelial cells, ligand stimulation of EGFR results in clathrin-mediated endocytosis and trafficking to the lysosome for degradation. This trafficking is regulated by multiple protein complexes, one of which involves a set of proteins called the Sorting Nexins (SNX) (reviewed in Bonifacino, J. S. & Hurley, J. H. Retromer. *Curr Opin Cell Biol* 20, 427-436, doi:10.1016/j.ceb.2008.03.009 (2008)). Of the multiple Sorting Nexin subgroups, one called the PX-BAR subgroup includes SNX1 and SNX2, which are the mammalian homologues of the yeast vacuolar protein Vsp5p. Vsp5p is an evolutionarily conserved protein that serves as a core component of the Retromer, a protein complex that regulates retrograde trafficking of transmembrane proteins. Within this complex SNX1 and SNX2 serve similar, but distinct roles. SNX2 promotes endosome to lysosome trafficking, while SNX1 promotes endosome to Golgi transport. The SNX proteins in the PX-BAR subgroup contain two key functional domains; a PH domain in their N-terminus that interacts with phosphatidylinositol moieties in the membrane and a BAR domain composed of coiled-coiled alpha-helixes that drive protein-protein interactions and can drive membrane remodeling. The BAR domain also drives SNX homo- and hetero-dimerization, key events in sorting and trafficking. SNX1 was originally identified as a protein that interacts with EGFR, and whose overexpression resulted in the degradation of activated EGFR. Interaction with SNX2 can also promote EGFR trafficking to the lysosome, indicating that SNX 1 and SNX2 dimers may need to be in balance to organize EGFR sorting. Subsequent studies demonstrated that the chronic overexpression of SNX1 results in the formation of extensive tubular networks due to membrane bending by the BAR domain, which could be leading to retrograde trafficking of cargo[18]. Different cell types and routes for EGFR endocytosis may utilize different sorting mechanisms, and our goal is to understand how these events are regulated in triple negative breast cancer, where EGFR has been shown to undergo retrotranslocation (modeled in FIG. 1). Previous work has shown that a loss of the polarity protein LGL results in rt-EGFR trafficking and an EGF dependent acquisition of cancer stem cell characteristics. These include induced expression of TAZ and Slug and EMT, and increased migration and survival in mammospheres. Similar phenotypes were also observed by a basolateral targeting mutation of EGFR that allowed it to be trafficked to the apical domain. In addition, interaction with the apically localized oncogene MUC1 similarly drives rt-EGFR. Together, these data indicate the rt-EGFR can be driven by multiple pathways, and all lead to cancer stem cell phenotypes in triple negative breast cancer.

Example 2 Sorting Nexin 1 BAR Domain Peptides Inhibit Cancer Cell Growth

To investigate rt-EGFR, the role of the Sorting Nexins to regulate EGFR trafficking to the lysosome for degradation was investigated. To determine if SNX1 domains could be therapeutically mimicked, three SNX1-based peptides were synthesized, each of which was generated in tandem with a Cell Penetrating Peptide domain (PTD-4) to allow for intracellular penetration[19] (SNX1.1, 1.2 and 1.3, FIG. 2A). The ability of each peptide to reduce cell survival in the triple negative breast cancer cell line BT20 was evaluated.

```
The sequence of SNX1.3 is
                                    (SEQ ID NO: 1)
YARAAARQARAKNHVIKYLETLLYSQQQLAKYWEAFL.
```

Upon identifying that SNX1.3 inhibits the growth of BT20 cells, the sequence was modified to increase its efficacy and these modified peptides were tested using the cell line MDA-MB-468, which has amplified EGFR (Filmus et al. 1985). Predicted peptide structure including negatively (blue) and positively (red) charged residues was used to guide the modifications (FIG. 2C). It was discovered that both C- and N-terminal peptide end-capping increased efficacy, so further work was done with peptide, cSNX1.3. As shown in FIG. 2A, cSNX1.3 has the sequence:

```
                                        (SEQ ID NO: 2)
Acetyl-YARAAARQARAKNHVIKYLETLLYSQQQLAKYWEAFL-NH2
```

wherein the N-terminal has been acetylated (CH3CO) and the C-terminal has been amidated (CONH2).

Example 3 cSNX1.3 Induces Tumor Regression in WAP-TGFα Transgenic Mice

To evaluate the impact of cSNX1.3 on an immune intact mouse model of cancer, WAP-TGFα mice were utilized, which is a transgenic line whose mammary gland tumors are EGFR dependent (Pochampalli, Bitler, and Schroeder 2007). Mice are continually bred to activate the pregnancy-dependent WAP promoter, which drives expression of the EGFR ligand Transforming Growth Factor alpha (TGFα) strictly to the mouse mammary glands. This model stochastically forms unifocal mammary adenocarcinomas through a process that begins with mammary hyperplasia, followed by tumor formation over approximately 8 months. Tumor-bearing females were established (as determined by forming a 100 $mm^3$ tumor that does not regress upon subsequent palpation) and then treated them with either cPTD4 peptide as a control or cSNX1.3. First, the potential toxicity of cSNX1.3 was evaluated by treating C57Bl/6J female mice with 5.0 or 10.0 μg/g body weight [3×/week, intravenous (IV) injections] with either cSNX1.3 or cPTD4 and weighing the animals for 3 days per week for 2 weeks (data not shown). No difference in weight or behavior or grooming was observed. Therefore 10 μg/g body weight was used for subsequent studies.

Figure 3:
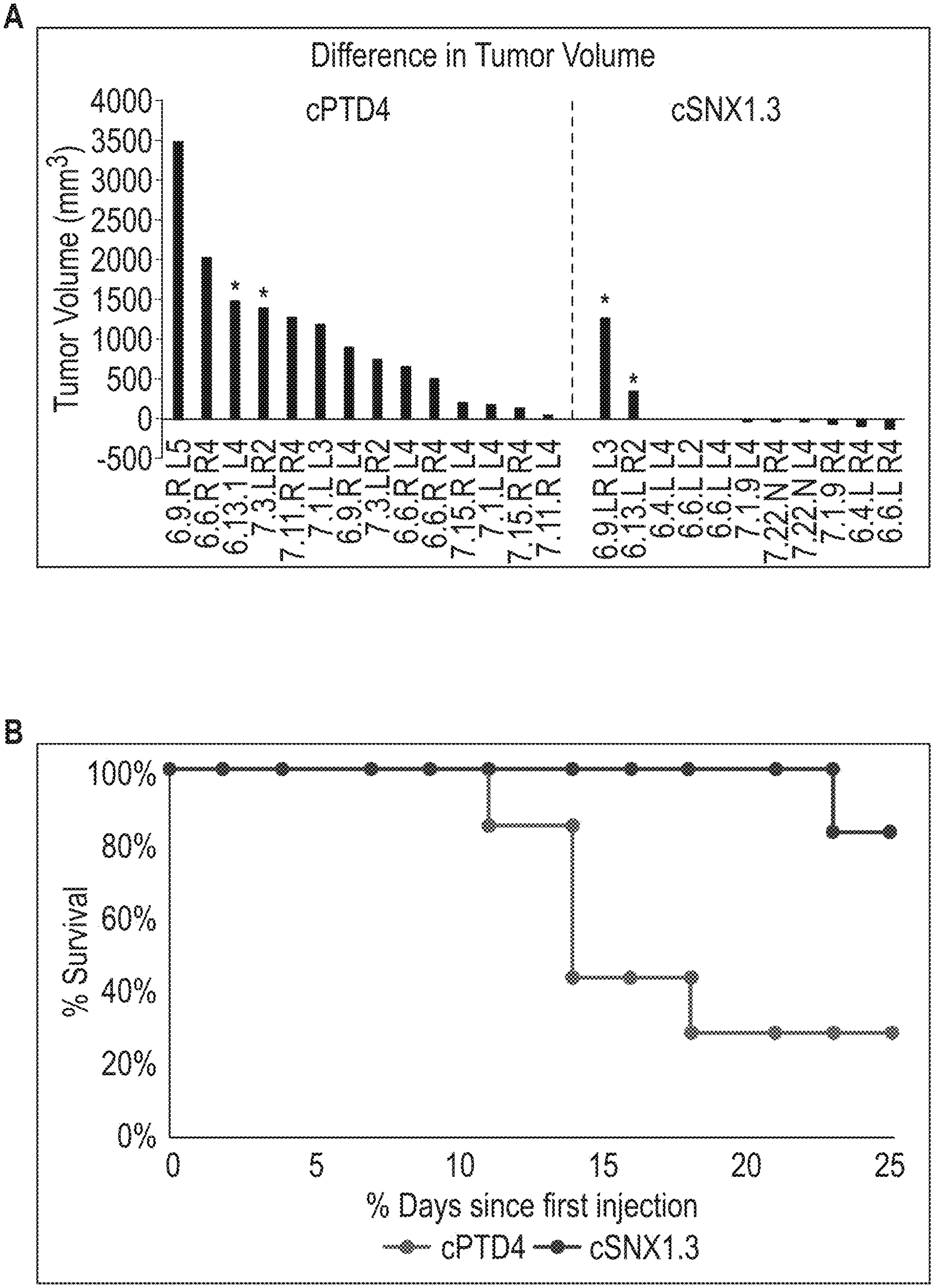
FIG. 3 shows cSNX1.3 driven tumor regression in WAP-TGFα transgenic mice. Mice were bred continuously to induce transgene expression and palpated weekly for tumor formation. Once tumors reached 100 $mm^3$, mice were entered into the study and given 10 μg/g body weight intravenous injections of either cPTD4 or cSNX1.3 3×/week. A. Changes in tumor size from entry into study until end of study are shown for each individual tumor, (*) indicate tumors that entered the study at size greater than 500 $mm^3$, all other tumors entered the study at ~100 $mm^3$. B. a Kaplan-Meier survival curve was generated showing when mice were sacrificed by either reaching tumor burden (2000 $mm^3$) or the end of the study (p=0.0002). C. Upon sacrifice tumors were harvested and fixed in 10% formalin and embedded in paraffin. Slides were stained with hematoxylin and eosin and imaged at 20×. D. Protein lysates were generated from tumors upon sacrifice and probed for the indicated proteins.

When tumors reached >100 $mm^3$, IV injections began at 3×/week, 10 μg/g body weight and tumors were measured 3×/week with calipers. Animals were injected for 4 weeks or until they reached maximal tumor burden, defined as a single tumor measuring 2000 $mm^3$. In the cPTD4 treated mice, the tumors (n=14) grew at an average of 30.8 $mm^3$/day while in the cSNX1.3 treated mice tumors (n=11) regressed at an average of 4 $mm^3$/day. Note that mice were weighed throughout the study and no impact on animal weight was observed in response to cSNX1.3 treatment. The WAP-TGFα is a spontaneous model in which each tumor arises and progresses in a heterogeneous fashion. Each tumor was evaluated separately to determine the overall impact of SNX1.3 treatment (FIG. 3A). Although cPTD4-treated tumors had a wide variety of tumor growth, all tumors grew by the end of the study. Conversely, 7/11 cSNX1.3-treated tumors regressed and 2/11 showed no change in tumor volume from the first to last measurement. Of note, 3 of the cSNX1.3 fully regressed as measured with calipers and confirmed during necropsy. Additionally, the 2 cSNX1.3 treated tumors that demonstrated growth through the study entered the study at greater than 500 $mm^3$. In this study, mice were sacrificed after 4 weeks of injections or once they reached tumor burden, represented by the Kaplin-Meyer graph (FIG. 3B). The increase in tumor burden was significantly different between cPTD4 and cSNX1.3 treated mice (p=0.0002). While 5/7 cPTD4 mice reached tumor burden before the end of the study only 1/6 cSNX1.3 treated mouse reached the maximal tumor burden.

At the end of the study, mice were sacrificed and tissues were collected and fixed in 10% buffered formalin or homogenized in tissue lysis buffer. Tissues were sectioned and evaluated for changes to tissue morphology in response to peptide treatment (FIG. 3C). Tissue morphology did not change, although in some of the tumors, they had regressed fully to a hyperplastic mammary gland at the end of the study. No changes to tissue architecture were observed in the normal mammary gland. Analysis of protein expression in treated tumors found an increase in cleaved PARP, indicating cSNX1.3 was inducing apoptosis as a means of tumor regression (FIG. 3D). Representative tumors from the PARP-cleavage positive (cSNX1.3-treated) and negative (cPTD4-treated) are shown (FIG. 3C).

Example 4 cSNX1.3 Displays Specificity for Wildtype EGFR and Cancer

Next, the efficacy of cSNX1.3 compared to the tyrosine kinase inhibitor Sapitinib (an EGFR-family specific TKI) was evaluated in several cell lines. The triple negative breast cancer cell lines MDA-MB-468 and BT20, the lung carcinoma cell lines H1975 and A549 and the immortalized breast epithelial line MCF10A with cSNX1.3, cPTD4 control, or Sapitinib (FIG. 4A) were used. While both cSNX1.3 and Sapitinib inhibited cell survival, cSNX1.3 was more effective than Sapitinib in the breast cancer cell lines MDA-MB-468 (IC50=7.5 μM) and BT20 (IC50=25 μM). Importantly, cSNX1.3 had almost no impact on normal immortalized cells (MCF10A), while Sapitinib was more effective at inhibiting cell growth in normal cells than in cancer cells. While cSNX1.3 had no effect on the H1975 cell line with an EGFR driver mutation in the kinase domain (T790M), it was more effective than Sapitinib in the A549 lung cancer line with wildtype EGFR.

Figure 4:
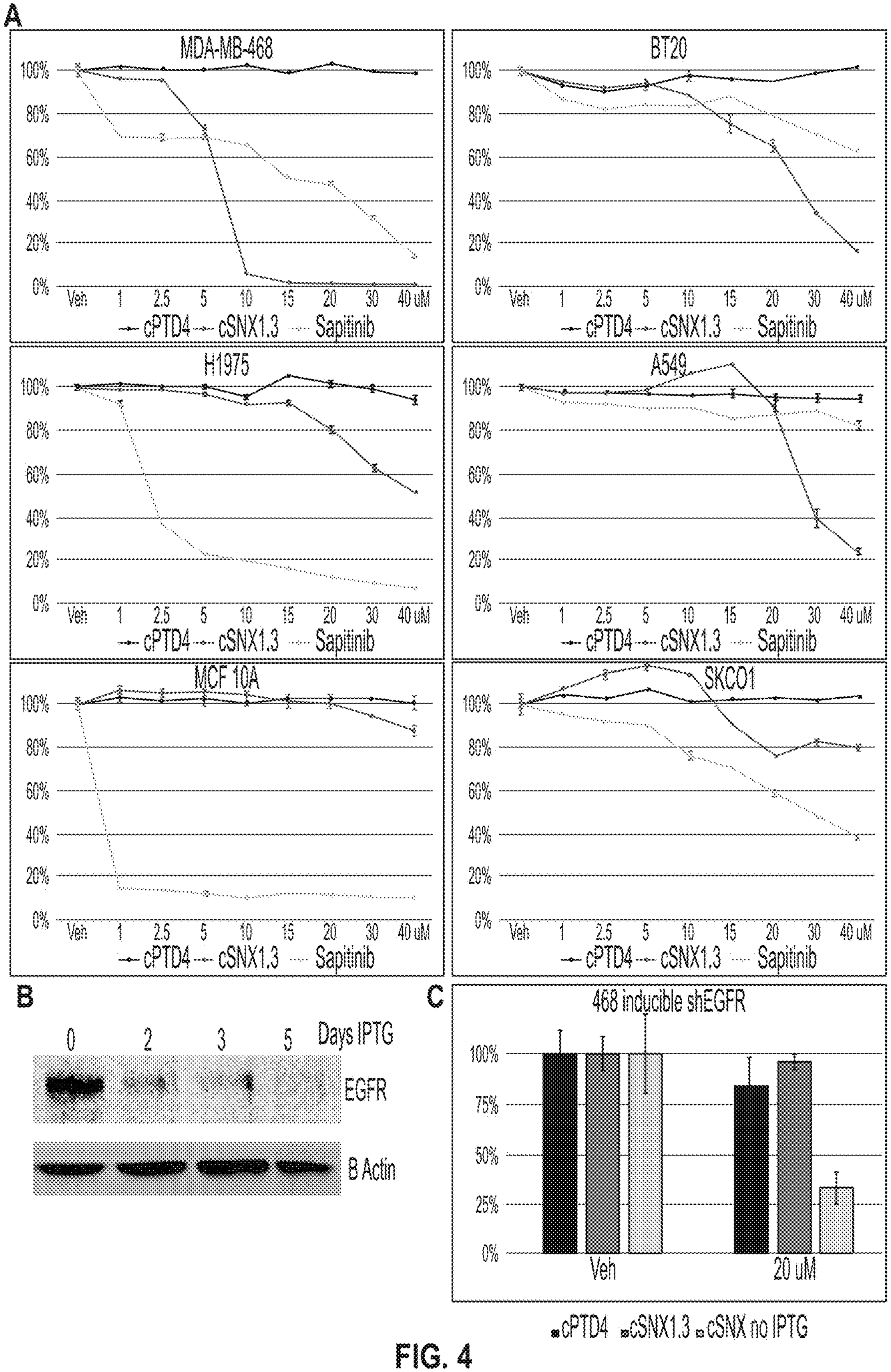
FIG. 4 shows cSNX1.3 peptide inhibits EGFR driven cancer cell viability. A. Cells were treated with the indicated concentration of cPTD4, cSNX1.3, or Sapitinib for 3 days and their viability was measured with an MTT assay. B. MDA-MD-468 cells were transduced with an IPTG inducible shEGFR targeted against the 3' UTR of EGFR. These cells were incubated with IPTG for the indicated number of days and lysates were generated to confirm knock down of EGFR. C. In tandem with B., cells were plated and incubated +/−IPTG for 2 days prior to drug treatment. After 2 days cells were treated with cPTD4 or cSNX1.3 and IPTG was reintroduced for 3 days, a second set of cSNX1.3 treated cells were grown in the absence of IPTG. After 5 days of IPTG and 3 days of peptide treatment viability was measured using an MTT assay.

To evaluate the specificity of cSNX1.3 for EGFR, the expression of endogenous EGFR was knocked down with a shRNA to the 3'UTR of EGFR in MDA-MB-468 cells. In these cells with reduced EGFR, cSNX1.3 lacked significant efficacy (FIGS. 4B and 4C). No effect on CHO cells that lack EGFR expression was observed. These data indicated that cSNX1.3 may be highly selective towards cancer expressing wildtype EGFR and we next worked towards understanding its mechanism of action.

Figure 5:
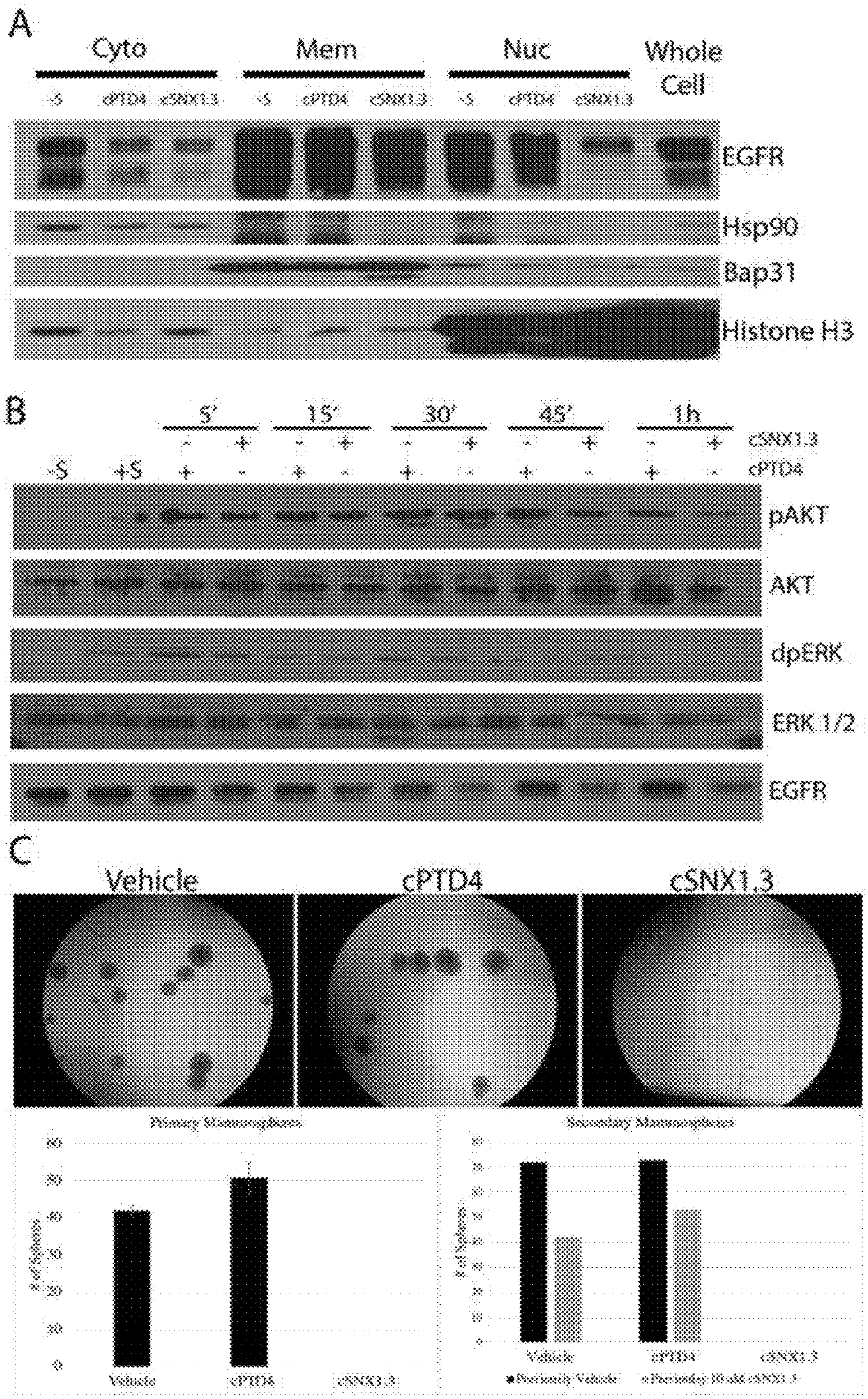
FIG. 5 shows cSNX1.3 inhibits nuclear EGFR and survival signaling. A. MDA-MB-468 cells were serum starved overnight then incubated with 20 ng/mL EGF and either cPTD4 or cSNX1.3 for 2 hours. Cells were then fractionated and verified by HSP90 cytosolic protein, Bap31 membrane protein, or HDAC nuclear protein. B. MDA-MB-468 cells were serum starved overnight then stimulated with EGF on ice for 10 minutes. Cells were then incubated with PTD4 or cSNX1.3 at 37° C. for the indicated time and protein lysates were taken. B. MDA-MB-468 cells were serum starved overnight then incubated on ice with 10 ng/mL EGF for 10 minutes. Excess EGF was removed and cells were incubated with either cPTD4 or cSNX1.3 for the indicated time, lysed and analyzed as indicated. C. BT20 mammospheres were grown for 1 week in the presence of either vehicle, cPTD4, or cSNX1.3 and trypsinized, counted and replated. After the second week, the number of secondary mammospheres were counted.

Example 5 cSNX1.3 Inhibits Trafficking of EGFR to the Nucleus and Signaling from Long Lived Endosomes As a mechanism for the induction of cell death, we next investigated the capacity of cSNX1.3 to reduce EGFR nuclear localization and AKT signaling. MDA-MB-468 were serum starved overnight then incubated with EGF and peptide for 2 hours to allow for nuclear localization of EGFR. Subcellular protein fractionation was then performed to isolate cytosolic, membrane, and nuclear protein fractions (FIG. 5A). A loss of nuclear localized EGFR upon treatment with cSNX1.3 was observed, which was verified by Histone H3 versus Bap31 and Hsp90 for nuclear, membrane and cytosolic fractions, respectively. These data indicate that the peptide is impacting the species of EGFR that undergoes nuclear translocation.

Next, the ability of cSNX1.3 to inhibit signal transduction events associated with EGFR endosomal signaling was evaluated. Evaluation of MDA-MB-468 cells treated with cSNX1.3 and PTD4 found that cSNX1.3 suppressed pAkt and dpERK activation, but only after an hour—there was no impact on immediate Akt or ERK activation (FIG. 5B, 15' versus 60'). This indicates cSNX1.3 was impacting EGF-dependent Akt activation from long-lived endosomes (late stage), but not from the cell surface (immediate).

To evaluate the effects of cSNX1.3 on cell survival, BT20 triple negative breast cancer cells were evaluated by a mammosphere assay, which allowed us to evaluate cell survival in a non-adherent environment. While cells grew and formed mammospheres under vehicle or PTD4 treatment, no mammospheres were formed upon treatment with cSNX1.3 (FIG. 5C). These spheres were then disassociated and re-plated to form secondary mammospheres, interestingly although no spheres were formed in the presence of cSNX1.3 enough viable single cells were collected to plate three wells of secondary mammospheres. Cells that had been previously treated with cPTD4 and cSNX1.3 were plated treated with vehicle, cPTD4, and cSNX1.3 for an additional week. As expected, both sets that were treated with cSNX1.3 on the second week showed no mammosphere formation. Interestingly, cells that had been treated with cSNX1.3 in the first week showed significant reduction of sphere formation while treated with cPTD4 and vehicle in the second week, indicating some minimal lasting effect of cSNX1.3 on these cells.

Example 6 cSNX1.3 Inhibits Ligand-Dependent Migration of Multiple RTKs

Figure 6:
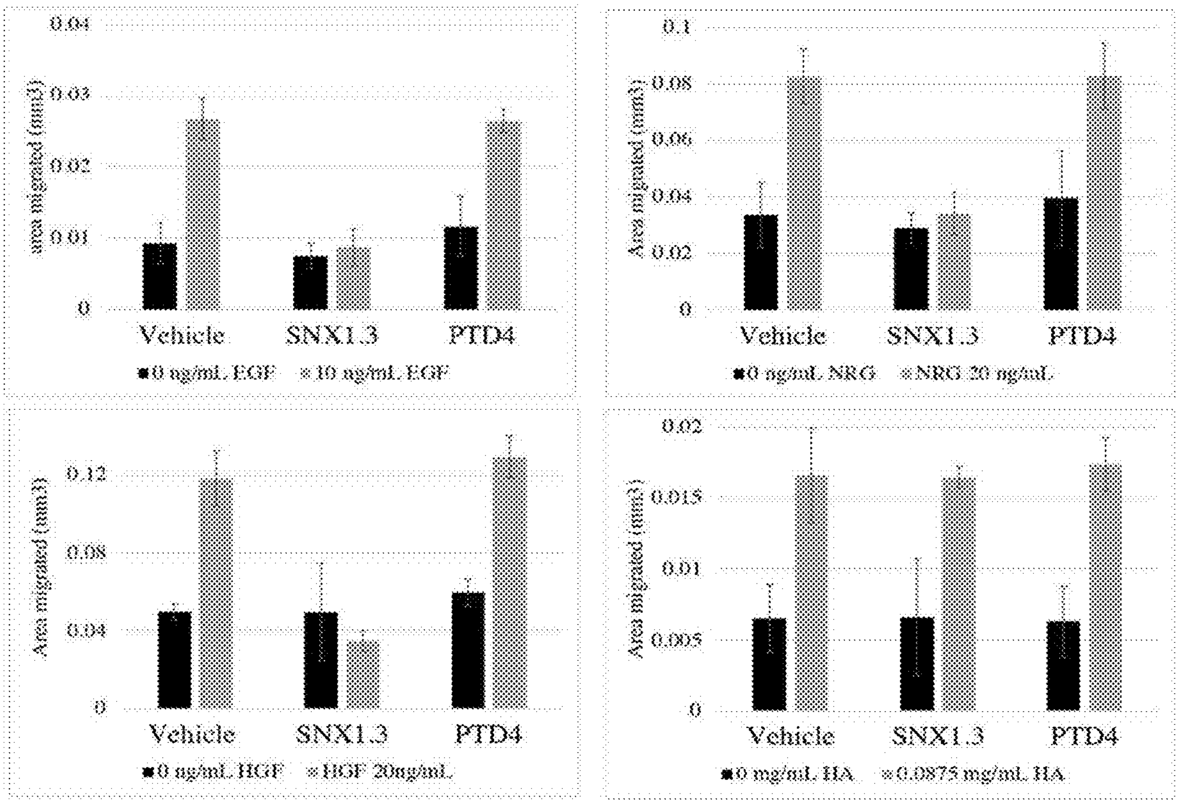
FIG. 6 shows SNX1.3 inhibits RTK driven 2D cell migration. BT20 triple negative breast cancer cells were treated with either cSNX1.3, PTD4 control or water (vehicle) and either EGF-, Neuregulin-1 (NRG), or Hepatic Growth Factor (HGF)-induced migration on plastic was allowed for 12 hours.
Figure 7:
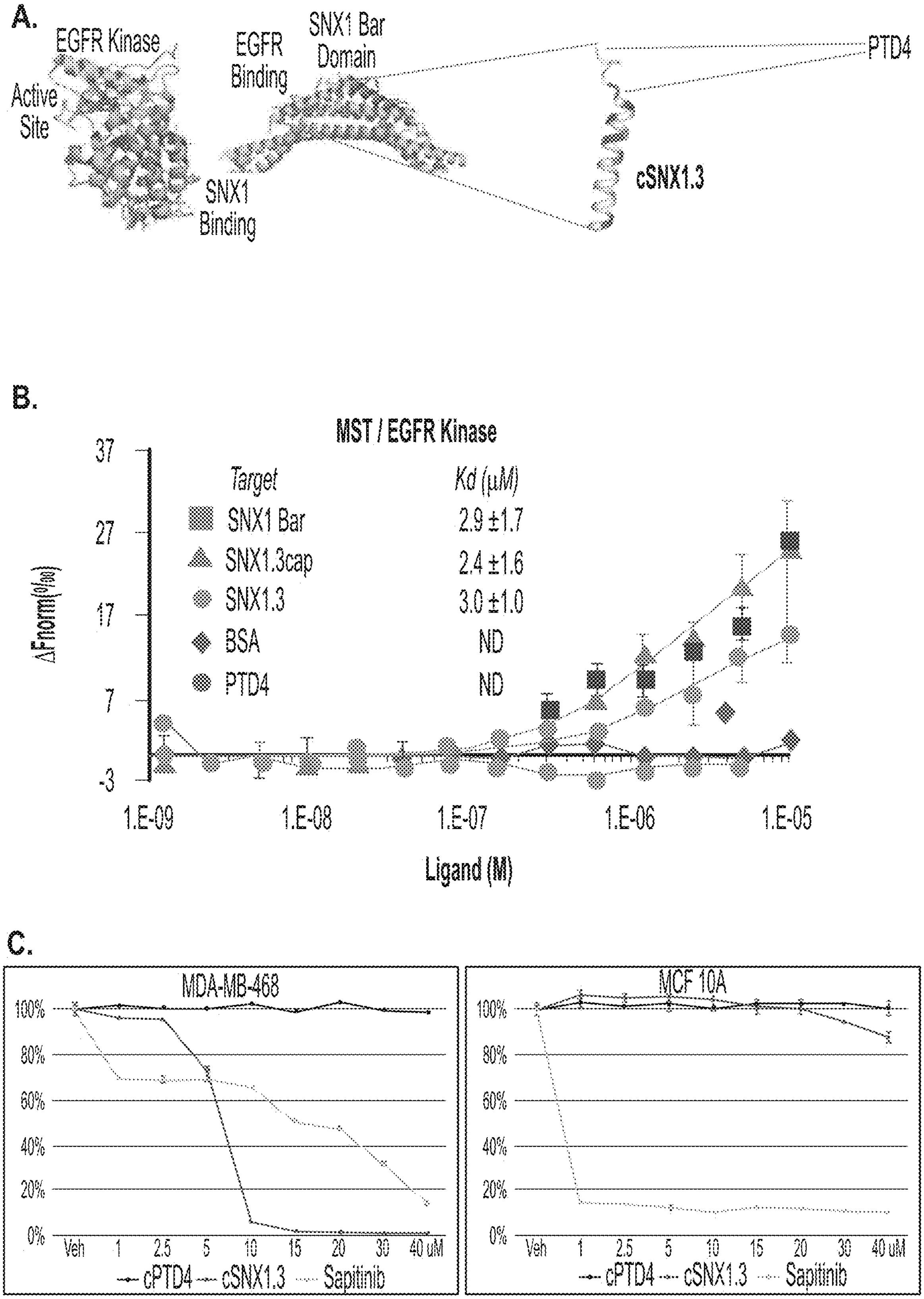
FIG. 7 shows that cSNX1.3 competitively inhibits binding of EGFR to SNX1, prevents TNBC survival, blocks nuclear EGFR localization, and induces tumor regression in WAP-TGFα mice. A. Ribbon drawing of EGFR kinase domain and SNX1 Bar domain. The domain of SNX1 from which cSNX1.3 is derived is indicated, and the PTD4 cell penetrating peptide is defined. B. MST binding curves of EFGR kinase domain (50 nM) with fluorescent dye attached through the His-tag titrated against the Bar domain, peptides cSNX1.3 (capped), cSNX1.3, and control PTD4, as well as control BSA. C. Cells were treated with cSNX1.3 compared to the EGFR tyrosine kinase inhibitor Sapitnib, and PTD4 control. D. Cells were treated similarly as in C., fractionated and evaluated for protein localization by immunoblot. E. WAP-TGFα mice were allowed to develop tumors, then treated for 4 weeks with cSNX1.3 or PTD4 control peptide (10 μg/g body weight, 3×/week, IV).

EGFR activity is known to promote the activity of other RTKs, including those in the EGFR family (HER2, HER3 and HER4) and the c-Met receptor (Puri and Salgia 2008; Linklater et al. 2016). Therefore, the ability of SNX1.3 to inhibit 2D migration was next evaluated, both in response to EGF as well as other migration-inducing ligands. Of note, sorting nexins have now been shown to regulate additional RTKs, including c-Met (Nishimura et al. 2014). Cells were plated on plastic and allowed to migrate into an artificial wound over 12 hours. Note that no impact on viability was observed via MTT in less than 24 hours, indicating any observed changes were not due to viability (data not shown). It is also found that while EGF induced significant migration of BT20 cells in the presence of the control PTD4 peptide, no migration was observed in the presence of SNX1.3 peptides (FIG. 6). To determine if this inhibitory effect was restricted to EGF-induced migration, the ability of SNX1.3 to impact neuregulin (NRG1) was also tested and hepatic growth factor (HGF)-induced migration. NRG is the ligand for HER3 and HER4, and HGF the ligand for the c-Met receptor, both of which are receptor tyrosine kinases. In addition, soluble hyaluronic acid (HA)-induced migration, the ligand for CD44, was also tested [a non-kinase membrane receptor that induces migration (Louderbough, Lopez, and Schroeder 2010)]. It is found that while SNX1.3 inhibited migration from all three RTKs, it did not block CD44 migration. Note that all receptors undergo endocytosis, with the RTKs primarily undergoing clathrin-dependent endocytosis, while CD44 endocytosis is clathrin-independent (Dutta and Donaldson 2015).

Example 7 Analysis of the Role of Nuclear EGFR to Alter NK Cell Activity and Macrophage Polarity Experiments were designed to determine whether treatment with cSNX1.3 can prevent nuclear EGFR from driving tumor growth and suppressing the immune system, which would in turn, result in tumor regression and activation of immune surveillance. The data shown in FIGS. 8, 9 and 10 highlight breast cancer cells treated with cSNX1.3 producing NK-activating antigens and suppressing PDL1 expression, as well as increased CTL and NK recruitment. Additionally, macrophages can be polarized into classically acting M1 or alternatively activated M2. The M2 macrophage is typically associated with promoting tumor progression while the M1 is tumor suppressive, with higher M1/M2 ratios signaling favorable outcomes. In FIG. 10, cSNX1.3 treated WAP-TGFα tumors showed a high M1/M2 ratio. Taken together, these data provide a strong rationale to evaluate the activation of immune cells as a mechanism for cSNX1.3.

Due to the increased leukocyte infiltration identified by histology of cSNX1.3-treated WAP-TGFα mice, NanoString analysis was performed using a panel that identifies alterations in immune regulators through localized analysis of transcript expression (PanCancer IO 360 Panel). Six tumor samples from either cSNX1.3 or PTD4 treated mice were analyzed and changes in gene expression determined. Evaluating all the differentially expressed genes in the NanoString analysis showed addition potential drivers of the cSNX1-3-mediated tumor regression (FIG. 8A). These include several immune/inflammatory genes (such as CD2, TLR, CD28, H2-M3, Ly6C1, cytokines, and chemokines) as well as genes that could impact the metastatic potential of the microenvironment (including collagen 11A1 and MM P12). NanoString bioinformatics analysis further identified that these changes could be due to an increase in Cytotoxic T lymphocytes (CTLs) in cSNX1.3-treated samples compared to PTD4 (FIG. 8B). Previous studies have found that EGFR and PDL1 surface expression are correlated with breast cancer immune suppression. Therefore, tumor lysates were prepared and evaluated for apoptosis and a loss of the negative immune checkpoint receptor PDL1 (FIG. 8C). A significant increase in apoptosis simultaneously with a decrease in overall PDL1 expression in response to cSNX1.3 treatment was observed. These changes could indicate an alteration from an immune-suppressive to an immune-surveilling microenvironment.

Figure 8:
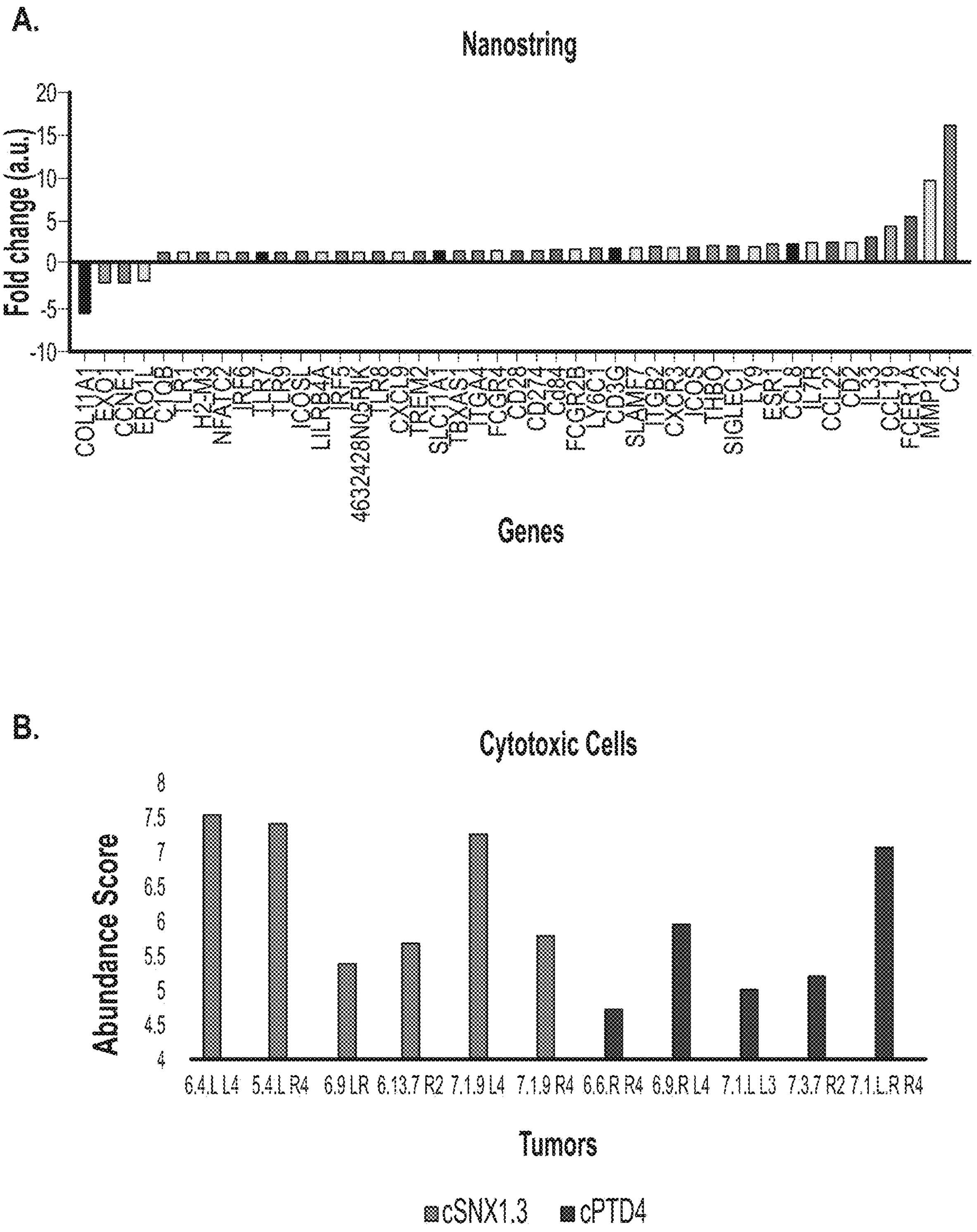
FIG. 8 shows cSNX1.3 treatment results in increased CTL activation and suppression of PDL1 expression in WAP-TGFα transgenic mice. A. Tumors (n=6 each treatment) from WAP-TGF mice as described in FIG. 1 were embedded and analyzed by NanoString. B. NanoString analysis identified increased CD8+ CTLs in cSNX1.3 (red) compared to PTD4 (blue) treated mice. C. Tumors were dissected, lysed, and analyzed for apoptosis by probing for cleaved PARP and PDL1 expression.
Figure 9:
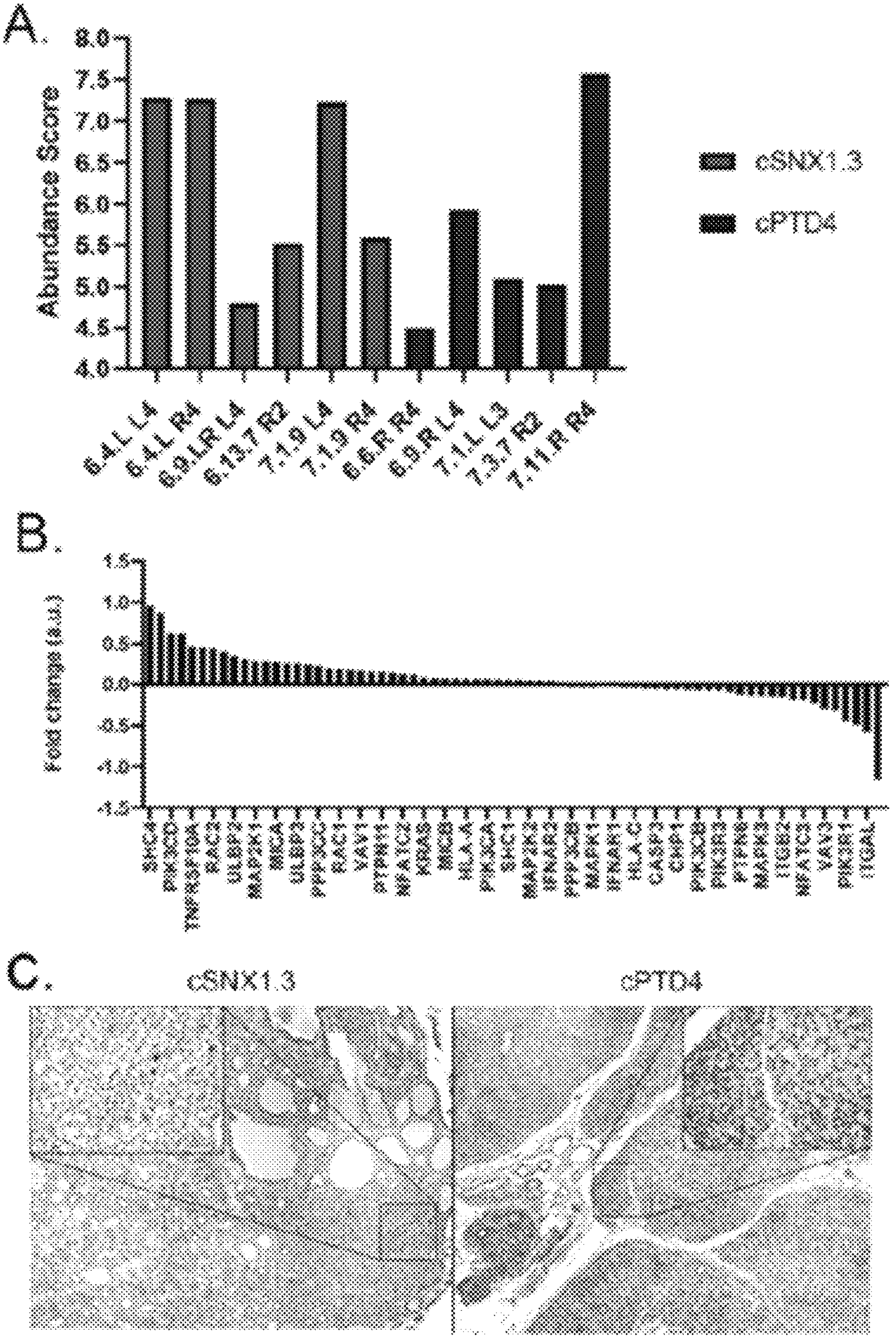
FIG. 9 shows Natural Killer Cell infiltration and associated genes are altered with SNX1.3. treatment. A. NanoString analysis for NK cells show an increase in WAP-TGFα tumor samples treated with cSNX1.3 (red) compared to PTD4 control (blue). B. RNAseq of cSNX1.3 treated MDA-MB-469 cells show alterations in NK-related genes. C. WAP-TGFα tumors treated with either SNX1.3 or cPTD4 were analyzed for NK cells using an anti-NKp46 antibody. Inset is 20×.
Figure 10:
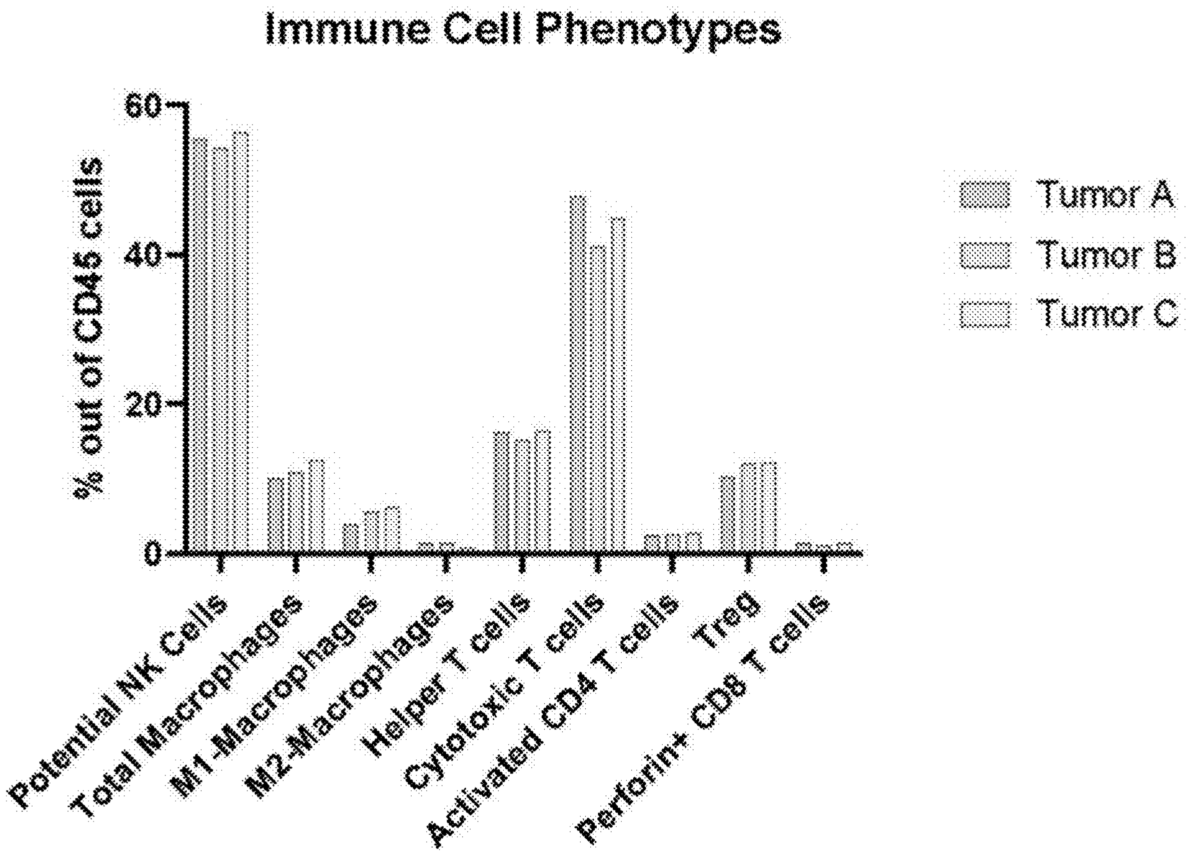
FIG. 10 shows WAP-TGFα tumors treated with cSNX1.3 have CTLs and NK cells. Preliminary immune profiling FACS analysis performed with the markers described in Example 1.

In addition to bioinformatics identification of CTLs in these tumors, similar analysis implicated recruitment of NK cells as well (FIG. 9). As a part of the innate immune system, NK cells should only be recruited if a change has occurred to display NK-activating antigens. While there are many such antigens expressed under a variety of immune modulation conditions, some are highly associated with activation of NK cells against cancers, such as ULBP2/3 or MICA/MICB32. Therefore, bulk RNAseq was performed on MDA-MB-468 cells (in triplicate, GeneWiz), with each gene's log expression centered and scaled and determined which NK genes are altered by cSNX1.3 treatment (FIG. 9B). cSNX1.3 treatment of these cells did not alter PDL1 expression, indicating that the changes observed from WAP-TGFα tumors treated with cSNX1.3 was not due to changes in the tumors themselves (FIG. 8). Alternatively, the NK activating antigens ULBP2, ULBP3, MICA and MICB were all increased upon cSNX1.3 treatment (FIG. 9B). WAP-TGFα tumors treated with cSNX1.3 versus PTD4 with anti-NKp46 antibodies were analyzed to detect NK cells. Significant NK cell infiltration into cSNX1.3 treated tumors was observed, but no NK cells were detected in PTD4-treated controls (FIG. 9C).

To begin to evaluate how these changes indicated by NanoString represented the immune microenvironment of these tumors, Immune Profiling was performed. For these studies, WAP-TGFα mice were allowed to form primary tumors>200 $mm^3$, then treated with IV injection of cSNX1.3 as described above. When tumors had regressed to ~100 $mm^3$ (after 1-2 weeks of treatment), tumor were excised, treated with collagenase and analyzed by FACS, using a 17-antibody panel to determine cell types present. Data was analyzed by first selecting for CD45+ cells to isolate leukocytes, then further gated based on markers specific to cells of both the adaptive and innate immune system. This preliminary analysis was done with 3 cSNX1.3-treated tumors, and the internal positive control of one spleen. Abundant CTLs, an increase of M1 (anti-tumor) macrophages over M2 (tumor promoting) macrophages, and helper T cells were found. Perhaps most strikingly, ~60% of the total CD45+ cells in the tumors were found to be NK cells (FIG. 10).

This result is used to focus the investigations into the role of cSNX1.3 in altering the immune microenvironment of breast cancer in the following three experiments:

1A) Define changes in gene expression by induced by nEGFR compared to normal EGFR signal transduction. The preliminary data indicate that cSNX1.3 suppresses transcriptional changes that drive the immune suppressive microenvironment, and it is hypothesized that this is due to inhibition of translocation of nEGFR. To test this, cSNX1.3-induced transcriptional changes are compared to transcription in cells that have been knocked down for endogenous EGFR and transduced with inducible $EGFR^{WT}$-GFP or EGFR in which nuclear localization signals (NLS) has been mutated ($EGFR^{\Delta NLS}$-GFP).

Figure 11:
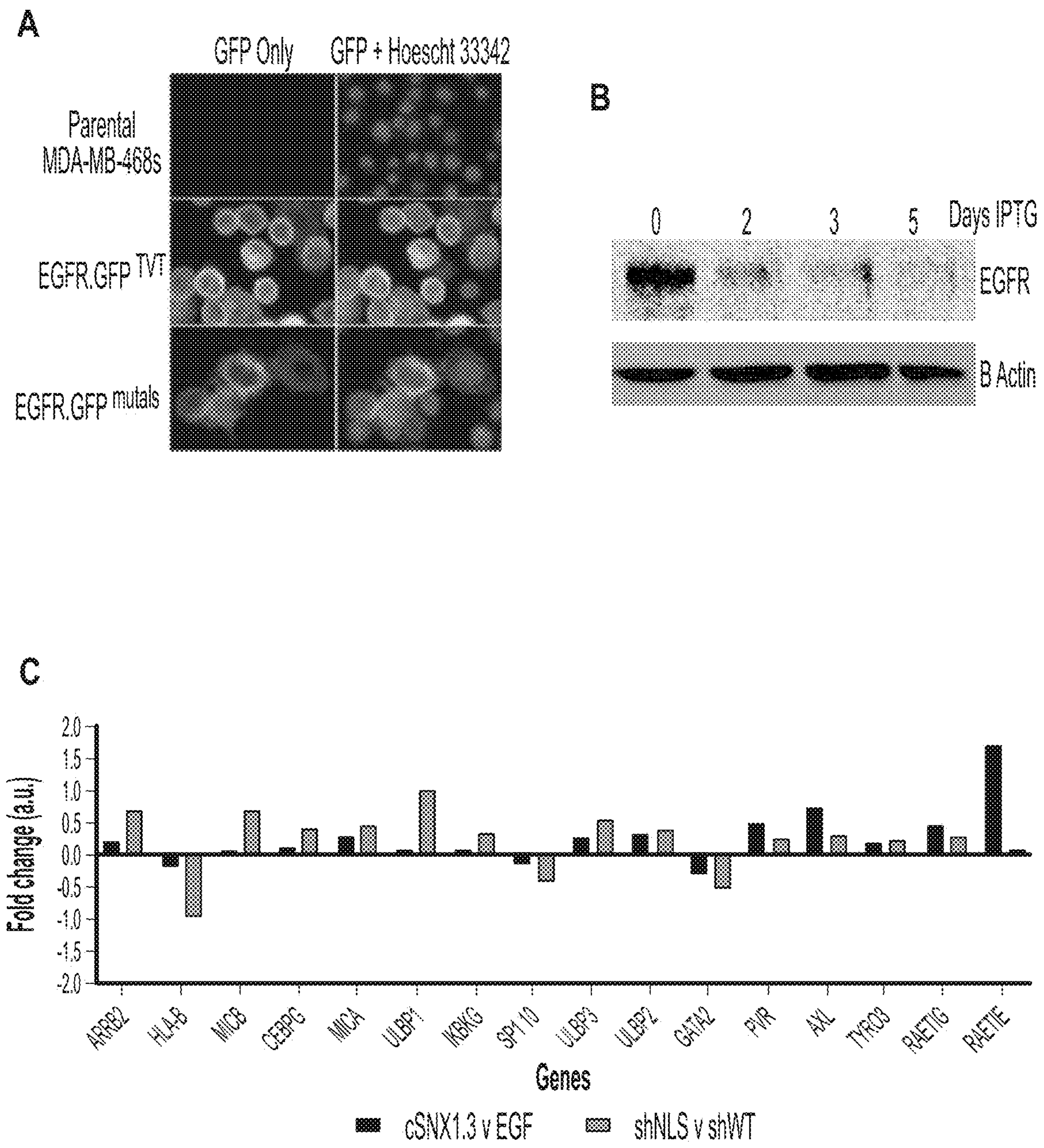
FIG. 11 shows that loss of nuclear EGFR induces NK cell antigens and activation. A. MDA-MB-468 cells were transfected with either wildtype EGFR-GFP or EGFR-GFP with the NLS sequence mutated and inactivated, resulting in a loss of nuclear EGFR. B. Cells are further treated with a shRNA against the 3'UTR of endogenous EGFR to reduce chances of mutant/wildtype EGFR dimerization. C. Bulk RNAseq was performed on the two populations and compared to cells treated with cSNX1.3 (+EGF) versus EGF alone, and changes in genes associated with NK cell activation were compared.

Experimental approach: the alteration in gene expression is evaluated by altering nuclear EGFR through both the use of EGFRwt-GFP vs EGFRDNLS-GFP cell models and cSNX1.3 treatment, performing RNAseq and ChIPseq and comparing genes regulated by nEGFR. This is performed in MDA-MB-468 cells as they have amplified EGFR which is translocated to the nucleus upon EGF treatment. Knockdown of endogenous EGFR has been validated using a 3'UTR shRNA, and then EGFR expression was replaced with either a EGFRwt-GFP vs EGFRDNLS-GFP and have altered the localization of EGFR in these cells (FIG. 11). A preliminary bulk RNAseq was performed on these cells and the EGFRWT-GFP/EGFRDNLS-GFP was compared to the gene changes upon cSNX1.3 treatment. Remarkable synergy was observed in the NK cell genes modified (FIG. 11). By comparing these two sets of modulation of nuclear EGFR (cSNX1.3 treatment and EGFRDNLS-GFP), it is ascertained that those changes are directly induced by nuclear EGFR.

1B) Define the immune profile of breast tumors in the presence/absence of SNX1.3 to determine the immune cell type that is recruited by SNX1.3 treatment. In a proof-of-principle experiment, a substantial population of CTLs and NK cells, with a M1/M2 macrophage population, was found in 3 tumors from one cSNX1.3-treated WAP-TGFα mouse. Further, there was a dramatic number of NK cells (greater than 50% of the CD45+ population, FIG. 10). The mechanism of how cSNX1.3 is altering the immune landscape is determined. Cytotoxic assays are performed to determine whether cSNX1.3 treatment promotes NK cytotoxity.

Immune Profiling: Tissues are digested and analyzed by FACS for the following immune markers: CD45 (lymphocytes), CD4 (helper T cells) CD3 (Pan T cell), CD25 (Activated T cells), CD8a (cytotoxic T cells), Ly6G (G-Myeloid Derived Suppressor Cells (MDSC), CD11 b (MDSC), Ly6C (M-M DSC), CD11C (Dendritic Cells), F4/80 (Macrophages), Granzyme B (Natural Killer (NK) and CD8 T cells), Arginase 1 (MDSC), Perforin (NK and CD8 Tcells), iNos (macrophages), TNFα (pro inflammatory cytokine), INFγ (pro inflammatory cytokine), FoxP3 (Treg). The samples are run on a Cytek Aurora full spectrum flow cytometer and are optimized for the mouse tissues (FIG. 10). In this analysis, potential NK cells are cells that were CD45+/CD3−/perforin+, while CTLs were CD45+/CD3+/CD8+. The data from this experiment is utilized to determine which immune cells are being recruited after SNX1.3 treatment. Statistical analysis will be performed, as described below.

Previously, it was found that treatment with cSNX and deleting the nuclear localization signal of EGFR induced the expression of NK activating antigens. If these changes lead to the activation of NK cells, it is expected that this is a driving factor of activating the immune system to induce tumor regression.

Example 8. Determine how Nuclear EGFR Alters IL1-Pathway Genes to Modulate the Immune Response Immune profiling of WAP-TGFα mice treated with cSNX1.3 showed an anti-tumor immune surveillance microenvironment (FIG. 10). The subset of cells observed, CTLs, NKs and M1 macrophages, typically work together in anti-tumor responses, with activation of M1 macrophages able to secrete cytokines that recruit NK cells and activating CTLs. These intercellular interactions can be heavily modified by IL1R signaling. SNX1.3 treatment of WAP-TGFα tumors induced the secretion of IL33, a cytokine that can activate CTLs and inhibit migration of macrophages. In addition, a decrease in expression of the immune suppressor PDL1 and increased infiltration of cytotoxic T lymphocytes and neutrophils in tumors from SNX1.3 treated WAP-TGFα mice is observed compared to control mice. Furthermore, RNAseq analysis demonstrates alteration of inflammatory pathways in SNX1.3 treated cells, indicating the potential for SNX1.3 to alter the immune microenvironment as part of its anti-tumor activity.

Figure 12:
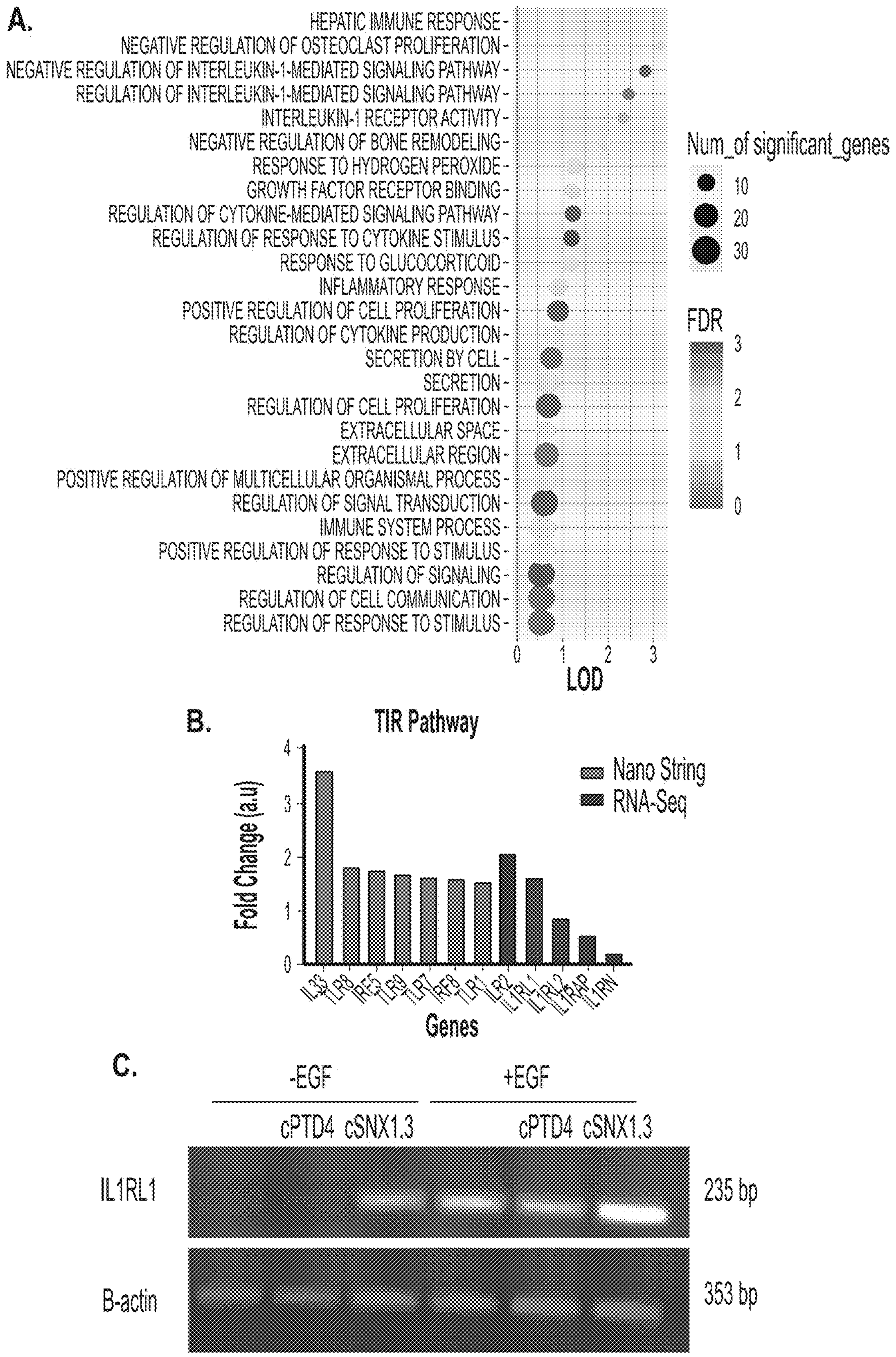
FIG. 12 shows inflammatory pathways are upregulated with cSNX1.3 treatment. A-C. MDA-MB-468 cells were serum starved (−EGF, S), then stimulated with 10 ng/ml of EGF and treated with 10 μM of the EGFR retrotranslocation inhibitor cSNX1.3, for 12 hours. A. A gene ontology enrichment bubble plot was produced, and the top 30 enriched GO terms are shown. Color indicates −1*log 10(FDR) for significance of overlap (the higher the more significant). X axis=log odds ratio for genes annotated to that GO term. B. subset of IL-1-related genes increased in response to cSNX1.3 treatment from NanoString (red) and RNAseq (blue). C. RT-PCR analysis of IL1RL1.

During the bulk RNAseq analysis, a gene ontology analysis was performed comparing the cSNX1.3 treated MDA-MB-468 cells to cPTD4 (3 replicates per treatment were analyzed using GeneWiz and the data queried). A significant impact on the immune response, especially IL-1 dependent pathways was identified (FIG. 12A). IL-1-specific genes were searched and an upregulation in several IL1R genes, including IL1R2, IL1RL1, IL1RL2, IL1RAP and IL1RN (FIG. 12B) were found. Importantly, of these, ILRL1 (also known as ST2) is the receptor for IL-33, which was found to be induced by NanoString. RT-PCR analysis of similarly treated cells identified IL1RL1 as upregulated by cSNX1.3 treatment (FIG. 12C). TLR (Toll-like receptors) are a part of the IL1R super-family and can work in concert to promote immune activation and increased expression of TLR1, TLR7, TLR8, TLR9 and the transcription factors activated by IL1R and TLR signaling, IRF5 and IRF8, were observed by NanoString (FIG. 8). It is hypothesized that the transient and targeted activation of the IL1/TLR pathway in the tumors may allow for the immune system to become active where previously these tumors were immune suppressive. Triple negative breast cancers with active EGFR pathways are clinically immune suppressive, and it is hypothesized that blocking nEGFR may allow for the utilization of immune targeting to treat these cancers. It is important to note that cSNX1.3 does not impact normal epithelium, which is predicted would limit off-target impacts of immune activation.

LITERATURE CITED

All literatures and patents or patent applications cited here or throughout the disclosure are hereby incorporated by reference in this disclosure.

1 Ponde, N., Brandao, M., El-Hachem, G., Werbrouck, E. & Piccart, M. Treatment of advanced HER2-positive breast cancer: 2018 and beyond. *Cancer Treat Rev* 67, 10-20, doi:10.1016/j.ctrv.2018.04.016 (2018).

2 Nakai, K., Hung, M. C. & Yamaguchi, H. A perspective on anti-EGFR therapies targeting triple-negative breast cancer. *Am J Cancer Res* 6, 1609-1623 (2016).

3 Greenwood, E. et al. Llgl1 prevents metaplastic survival driven by epidermal growth factor dependent migration. *Oncotarget* 7, 60776-60792, doi:10.18632/oncotarget.11320 (2016).

4 Syrkina, M. S., Vassetzky, Y. S. & Rubtsov, M. A. MUC1 Story: Great Expectations, Disappointments and the Renaissance. *Curr Med Chem* 26, 554-563, doi:10.2174/0929867324666170817151954 (2019).

5 Lo, H. W. et al. Nuclear interaction of EGFR and STAT3 in the activation of the iNOS/NO pathway. *Cancer Cell* 7, 575-589, doi:10.1016/j.ccr.2005.05.007 (2005).
6 Hung, L. Y. et al. Nuclear epidermal growth factor receptor (EGFR) interacts with signal transducer and activator of transcription 5 (STAT5) in activating Aurora-A gene expression. *Nucleic Acids Res* 36, 4337-4351, doi:10.1093/nar/gkn417 (2008).
7 Shi, Y. et al. Nuclear EGFR-PKM2 axis induces cancer stem cell-like characteristics in irradiation-resistant cells. *Cancer Lett* 422, 81-93, doi:10.1016/j.canlet.2018.02.028 (2018).
8 Brand, T. M. et al. Nuclear EGFR as a molecular target in cancer. *Radiother Oncol* 108, 370-377, doi:10.1016/j.radonc.2013.06.010 (2013).
9 Traynor, A. M. et al. Nuclear EGFR protein expression predicts poor survival in early stage non-small cell lung cancer. *Lung Cancer* 81, 138-141, doi:10.1016/j.lungcan.2013.03.020 (2013).
10 Waks, A. G. & Winer, E. P. Breast Cancer Treatment: A Review. *JAMA* 321, 288-300, doi:10.1001/jama.2018.19323 (2019).
11 Maisel, S., Broka, D. & Schroeder, J. Intravesicular epidermal growth factor receptor subject to retrograde trafficking drives epidermal growth factor-dependent migration. *Oncotarget* 9, 6463-6477, doi:10.18632/oncotarget.23766 (2018).
12 Shelly, M. et al. Polar expression of ErbB-2/HER2 in epithelia. Bimodal regulation by Lin-7. *Dev Cell* 5, 475-486 (2003).
13 Sorkin, A. & Goh, L. K. Endocytosis and intracellular trafficking of ErbBs. *Exp Cell Res* 314, 3093-3106 (2008).
14 Bonifacino, J. S. & Hurley, J. H. Retromer. *Curr Opin Cell Biol* 20, 427-436, doi:10.1016/j.ceb.2008.03.009 (2008).
15 Gullapalli, A. et al. A role for sorting nexin 2 in epidermal growth factor receptor down-regulation: evidence for distinct functions of sorting nexin 1 and 2 in protein trafficking. *Mol Biol Cell* 15, 2143-2155, doi:10.1091/mbc.E03-09-0711 (2004).
16 Teasdale, R. D. & Collins, B. M. Insights into the PX (phox-homology) domain and SNX (sorting nexin) protein families: structures, functions and roles in disease. *Biochem J* 441, 39-59, doi:10.1042/BJ20111226 (2012).
17 Kurten, R. C., Cadena, D. L. & Gill, G. N. Enhanced degradation of EGF receptors by a sorting nexin, SNX1. *Science* 272, 1008-1010, doi:10.1126/science.272.5264.1008 (1996).
18 Carlton, J. et al. Sorting nexin-1 mediates tubular endosome-to-TGN transport through coincidence sensing of high-curvature membranes and 3-phosphoinositides. *Curr Biol* 14, 1791-1800, doi:10.1016/j.cub.2004.09.077 (2004).
19 Bitler, B. G. et al. Intracellular MUC1 peptides inhibit cancer progression. *Clin Cancer Res* 15, 100-109, doi:10.1158/1078-0432. CCR-08-1745 (2009).
20 Dutta, D. & Donaldson, J. G. Sorting of Clathrin-Independent Cargo Proteins Depends on Rab35 Delivered by Clathrin-Mediated Endocytosis. *Traffic* 16, 994-1009, doi:10.1111/tra.12302 (2015).
21 Bitler, B. G., Goverdhan, A. & Schroeder, J. A. MUC1 regulates nuclear localization and function of the epidermal growth factor receptor. *J Cell Sci* 123, 1716-1723, doi:10.1242/jcs.062661 (2010).
22 Pochampalli, M. R., el Bejjani, R. M. & Schroeder, J. A. MUC1 is a novel regulator of ErbB1 receptor trafficking. *Oncogene* 26, 1693-1701, doi:10.1038/sj.onc.1209976 (2007).
23 Wang, Q., Yang, S., Wang, K. & Sun, S. Y. MET inhibitors for targeted therapy of EGFR TKI-resistant lung cancer. *J Hematol Oncol* 12, 63, doi:10.1186/s13045-019-0759-9 (2019).
24 Horm, T. M., Bitler, B. G., Broka, D. M., Louderbough, J. M. & Schroeder, J. A. MUC1 drives c-Met-dependent migration and scattering. *Mol Cancer Res* 10, 1544-1554, doi:10.1158/1541-7786.MCR-12-0296 (2012).
25 Maisel, S. A. et al. Stapled EGFR peptide reduces inflammatory breast cancer and inhibits additional HER-driven models of cancer. *J Transl Med* 17, 201, doi:10.1186/s12967-019-1939-7 (2019).
26 Pochampalli, M. R., Bitler, B. G. & Schroeder, J. A. Transforming growth factor alpha dependent cancer progression is modulated by Muc1. *Cancer Res* 67, 6591-6598, doi:10.1158/0008-5472. CAN-06-4518 (2007).
27 Sandgren, E. P. et al. Inhibition of mammary gland involution is associated with transforming growth factor a but not c-myc-induced tumorigenesis in transgenic mice. *Cancer Research* 55, 3915-3927 (1995).
28 Hart, M. R., Su, H. Y., Broka, D., Goverdhan, A. & Schroeder, J. A. Inactive ERBB receptors cooperate with reactive oxygen species to suppress cancer progression. *Mol Ther* 21, 1996-2007, doi:10.1038/mt.2013.196 (2013).
29 Lopez, J. I. et al. CD44 attenuates metastatic invasion during breast cancer progression. *Cancer Res* 65, 6755-6763, doi:10.1158/0008-5472.CAN-05-0863 (2005).
30 Lacerda, L. et al. Mesenchymal stem cells mediate the clinical phenotype of inflammatory breast cancer in a preclinical model. *Breast Cancer Res* 17, 42, doi:10.1186/s13058-015-0549-4 (2015).
31 Crunkhorn, S. Anticancer drugs: Stapled peptide reactivates p53. *Nat Rev Drug Discov* 12, 741, doi:10.1038/nrd4133 (2013).

We claim:

1. A composition comprising a molecule that binds to an epidermal growth factor receptor (EGFR) in a cell, wherein said molecule inhibits retrotranslocation of the EGFR to nucleus of the cell, and wherein said molecule comprises a peptide having a sequence at least 90% identical to the sequence of SEQ ID NO: 1, or at least 90% identical to the sequence of SEQ ID NO: 2.

2. The composition of claim 1, wherein the molecule binds to the kinase domain of the EGFR.

3. The composition of claim 1, wherein the molecule inhibits migration driven by a second receptor tyrosine kinase (RTK), said second receptor tyrosine kinase being different from EGFR.

4. The composition of claim 3, wherein said second RTK undergoes clathrin-dependent endocytosis, and the RTK is a member selected from the group consisting of C-Met, HER3 and HER4.

5. The composition of claim 1, wherein the molecule causes regression of tumors and does not cause observable toxicity in normal non-cancer cells.

6. The composition of claim 1, wherein said molecule is a peptide having the sequence of SEQ ID NO: 1 or a peptide having the sequence of SEQ ID NO: 2.

7. A method for treating breast cancer in a subject in need thereof, comprising delivering a composition to a subject, the composition comprising a therapeutically effective amount of a molecule that binds to an epidermal growth factor receptor (EGFR) in a cell of the subject, wherein said molecule inhibits retrotranslocation of the EGFR to nucleus of the cell, and wherein said molecule comprises a peptide having a sequence at least 90% identical to the sequence of SEQ ID NO: 1, or at least 90% identical to the sequence of SEQ ID NO: 2.

8. The method of claim 7, wherein the cancer is a triple-negative breast cancer, or an EGFR-dependent breast cancer.

9. The method of claim 8, wherein the dosage is from 1 mg to 200 mg per kg body weight of the subject.

10. The method of claim 7, wherein the molecule inhibits migration driven by a second receptor tyrosine kinase (RTK), wherein the RTK is a member selected from the group consisting of C-Met, HER3 and HER4 and said second receptor tyrosine kinase (RTK) is different from EGFR.

11. The method of claim 7, wherein the molecule causes regression of tumors without causing observable toxicity in normal non-cancer cells.

12. The method of claim 7, wherein said molecule is a peptide having the sequence of SEQ ID NO: 1, or a peptide having the sequence of SEQ ID NO: 2.

13. The method of claim 7, wherein said molecule activates immune cells in the subject, the immune cells being at least one member selected from the group consisting of Cytotoxic T Lymphocytes (CTLs), Natural Killer cells (NK cells) and macrophages.

14. The method of claim 13, wherein the activated immune cells induce tumor killing and prevent metastatic spread of the cancer.

15. The method of claim 7, wherein the molecule at said therapeutically effective amount increases the M1/M2 macrophage polarity (M1 being tumor suppressive and M2 being tumor promoting).

16. A pharmaceutical composition comprising a therapeutically effective amount of a molecule that binds to an epidermal growth factor receptor (EGFR) in a cell of the subject, wherein said molecule inhibits retrotranslocation of the EGFR to nucleus of the cell, and wherein said molecule comprises a peptide having a sequence at least 90% identical to the sequence of SEQ ID NO: 1, or at least 90% identical to the sequence of SEQ ID NO: 2.

17. The pharmaceutical composition of claim 16, wherein said molecule is a peptide having the sequence of SEQ ID NO: 1, or a peptide having the sequence of SEQ ID NO: 2.

* * * * *